(12) United States Patent
Discher et al.

(10) Patent No.: US 7,217,427 B2
(45) Date of Patent: *May 15, 2007

(54) POLYMERSOMES AND RELATED ENCAPSULATING MEMBRANES

(75) Inventors: Dennis E. Discher, Philadelphia, PA (US); Bohdana M. Discher, Philadelphia, PA (US); You-Yeon Won, West Lafayette, IN (US); James C-M Lee, Columbia, MO (US); Daniel A. Hammer, Villanova, PA (US); Frank Bates, Minneapolis, MN (US)

(73) Assignees: The Trustees of the University of Pennsylvania, Philadelphia, PA (US); Regents of the University of Minnesota, Minneapolis, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/882,816

(22) Filed: Jul. 1, 2004

(65) Prior Publication Data
US 2005/0048110 A1 Mar. 3, 2005

(51) Int. Cl.
*A61K 9/127* (2006.01)

(52) U.S. Cl. ............ 424/450; 424/1.21; 424/9.321; 424/9.51; 424/417; 424/489; 424/502; 428/402.2; 264/4.1; 264/4.3

(58) Field of Classification Search ............ 424/450, 424/1.21, 9.321, 9.51, 417, 489, 502; 428/402.2; 264/4.1, 4.3, 4.6
See application file for complete search history.

(56) References Cited

U.S. PATENT DOCUMENTS

| | | | | |
|---|---|---|---|---|
| 5,227,170 | A | * | 7/1993 | Sullivan .................. 424/450 |
| 5,595,756 | A | * | 1/1997 | Bally et al. .............. 424/450 |
| 6,835,394 | B1 | * | 12/2004 | Discher et al. .......... 424/450 |

OTHER PUBLICATIONS

Alberts et al , *Molecular Biology of the Cell*, 3rd ed., pp. 489-493; pp. 800-801, Garland Publishing, Inc., New York (1994).
Angelova et al., "Preparation of giant vesicles by external AC electric fields.Kinetics and applications", *Prog. Coll. Polym. Sci.* 89:127 (1992).

(Continued)

*Primary Examiner*—Gollamudi S. Kishore
(74) *Attorney, Agent, or Firm*—Evelyn H. McConathy, Esq.; Montgomery, McCracken, Walker & Rhoads, LLP

(57) ABSTRACT

The present invention provides biocompatible vesicles comprising semi-permeable, thin-walled encapsulating membranes which are formed in an aqueous solution, and which comprise one or more synthetic super-amphiphilic molecules. When at least one super-amphiphile molecule is a block copolymer, the resulting synthetic vesicle is termed a "polymersome." The synthetic, reactive nature of the amphiphilic composition enables extensive, covalent cross-linking of the membrane, while maintaining semi-permeability. Cross-linking of the polymer building-block components provides mechanical control and long-term stability to the vesicle, thereby also providing a means of controlling the encapsulation or release of materials from the vesicle by modifying the composition of the membrane. Thus, the encapsulating membranes of the present invention are particularly suited for the reliable, durable and controlled transport, delivery and storage of materials.

8 Claims, 14 Drawing Sheets

OTHER PUBLICATIONS

Bates, "Polymer-Polymer Phase Behavior", *Science* 251:898 (1991).

Bloom et al., "Physical properties of the fluid lipid-bilayer component of cell membranes: a perspective", *Q. Rev. Biophys.* 24 (3):293 (1991).

Chaieb et al. "Spontaneous curvature-induced pearling instability", *Phys. Rev. E* 58:7733 (1998).

Cevc & Lasic in *Handbook of Biological Physics*, Chaps. 9-10, (1995).

Cornelissen et al., "Helical Superstructures from Charged Poly(styrene)-Poly(isocyanodipeptide) Block Copolymers", *Science* 280:1427 (1998).

Ding and Lieu, "Water-Soluble Hollow Nanospheres as Potential Drug Carriers", *J. Phys. Chem. B* 102:6107-6113 (1998).

Discher et al., "Polymersomes: Tough Vesicles Made from Diblock copolymers", *Science* 284:1143 (May 14, 1999).

Dobereiner et al , "Mapping vesicle shapes into the phase diagram: A comparison of experiment and theory", *Phys. Rev. E* 55:4458 (1997).

Deuling et al., "The Curvature Elasticity of Fluid Membranes: A Catalogue of Vesicle Shapes", *J. Phys.* 37:1335 (1976).

Evans and Needham, "Physical Properties of Surfactant Bilayer Membranes: Thermal Transitions, Elasticity, Rigidity, Cohesion, and Colloidal Interactions", *J. Phys. Chem.* 91, 4219 (1987).

Evans et al., "Entropy-Driven Tension and Bending Elasticity in Condensed-fluid Membranes", *Phys. Rev. Lett.* 64 (17): 2094 (1990).

Fendler et al., "Polymerized Surfactant Vesicles: Novel Membrane Mimetic Systems", *Science* 223:888 (1984).

Harasym et al., "Intratumor distribution of doxorubicin following i.v. administration of drug encapsulated in egg phosphatidylcholine/ cholesterol liposomes", *Cancer Chemother. Pharmacol.* 40:309 (1997).

Hajduk et al., "Complex Phase Behavior in Aqueous Solutions of Poly(ethylene oxide)-Poly(ethylethylene) Block Copolymers", *J. Phys. Chem. B* 102:4269 (1998).

Helfrich et al, "Undulations, Steric Interactions and Cohesion of Fluid Membranes", *Il Nuovo Cimento* 3D:137 (1984).

Henselwood et al., "Water-Soluble Porous Nanospheres", *Macromolecules* 31:4213 (1998).

Hentze et al., "Lyotropic Mesophases of Poly(ethylene oxide)-b-poly(butadiene) Diblock Copolymers and Their Cross-Linking To Generate Ordered Gels", *Macromolecules* 32 (18): 5803-5809 (Jul. 30, 1999).

Hillmyer and Bates, "Synthesis and Characterization of Model Polyalkane-Poly(ethylene oxide) Block Copolymers", *Macromolecules* 29: 6994 (1996).

Hillmyer et al., "Complex Phase Behavior in Solvent-Free Nonionic Surfactants", *Science* 271:976-978 (1996).

J. Israelachvili, "Fluid-Like Structures and Self-Assembling Systems: Micelles, Bilayers and Biological membranes", Part 3, $2^{nd}$ ed., *Intermolecular and Surface Forces* (1995).

Koltover et al., An Inverted Hexagonal Phase of Cationic Liposome-DNA Complexes Related to DNA Release and Delivery, *Science* 281:78 (1998).

Komatsu et al., "Solid Vesicle Membrane Made of *meso*-Tetrakis[(bixinyiamino)-*o*-phenyl]porphyrins", *J. Am. Chem. Soc.* 119:11660 (1997).

Lin et al., "Cryogenic Electron Microscopy of Rodlike or Wormlike Micelles in Aqueous Solutions of Nonionic Surfactant Hexaethylene Glycol Monohexadecyl Ether", *Langmui*, 8: 2200 (1992).

Lipowsky and Sackmann, Eds., "Structure and Dynamics of Membranes from Cells to Vesicles", *Handbook of Biological Physics*, vol. 1, Chap. 1-4, 5-10 (Elsevier Science, Amsterdam, 1995).

Liu and O'Brien, "Cross-Linking Polymerization in Two-Dimensional Assemblies: Effect of the Reactive Group Site", *Macromolecules* 32:5519-5524 (Aug. 7, 1999).

Longo et al., "Interaction of the Influenza Hemagglutinin Fusion Peptide with Lipid Bilayers: Area Expansion and Permeation", *Biophys. J.* 73:1430 (1997).

Mueller et al., "Light-Stimulated Destabilization of PEG-Liposomes", *Polymer Preprints* (ACS) 40(2): 205-206 (Aug. 22, 1999).

Needham et al., "The Mechanochemistry of Lipid Vesicles Examined by Micropipet Manipulation Techniques", in *Vesicles*, M. Rosoff, Ed. (Dekker, New York), Chap. 9 (1996).

Needham et al., "Elastic Deformation and failure of lipid bilayer membranes containing cholesterol", *Biophys. J.* 58:997 (1990).

Netz et al., "Pore formation and rupture in fluid bilayers", *Phys. Rev. E* 53 (4): 3875 (1996).

Petrov, A.G. and Bivas, I., "Elastic and Flexoelectric Aspects of Out-of-Plant Fluctuations in biological and Model Membranes", *Prog. Surf. Sci.* 18:359 (1984).

Schmid-Schoenbein et al., "Spectrin, Red Cell Shape and Deformability", *Blut* 52(3):131 (Springer-Verlag 1986).

Seifert et al., "Shape transformations of vesicles: Phase diagram for spontaneous-curvature and bilayer-coupling models", *Phys. Rev. A* 44:1182 (1991).

Sisson et al., "Cross-Linking Polymerizations in Two -Dimensional Assemblies", *Macromolecules* 29:8321 (1996).

Svetina et al., "Membrane bending energy and shape determination of phospholipid vesicles and red blood cells", *Eur. Biophys J*, 17:101 (Springer-Verlag 1989).

Szleifer et al., "Curvature Elasticity of Pure and Mixed Surfactant Films", *Phys. Rev. Lett.* 60(19): 1966 (1988).

Stefely et al, "Permeability Characteristics of Lipid Bilayers from Lipoic Acid Derived Phosphatidylcholines: Comparison of Monomeric, Cross-Linked and Non-Cross-Lined Polymerized Membranes", *J. Am. Chem. Soc.* 110:7463-7469 (1988).

Uchegbu et al., "Polymeric Chitosan-based Vesicles for Drug Delivery", *J. Pharm. Pharmacol.* 50:453 (1998).

Warriner et al., "Lamellar Biogels: fluid-Membrane-Based Hydrogels Containing Polymer Lipids", *Science* 271: 969 (1996).

Won et al., "Giant Wormlike Rubber Micelles", *Science* 283:960-3 (Feb. 12, 1999).

Yu et al., "Morphogenic Effect of Solvent on Crew-Cut Aggregates of Amphiphilic Diblock Copolymers", *Macromolecules* 31:1144 (1998).

\* cited by examiner

POLYMERSOMES AND RELATED ENCAPSULATING MEMBRANES

GOVERNMENT SUPPORT

This work was supported in part by grants from the National Science Foundation, grant numbers DMR96-32598 and DMR 98-09364, and also by grants from the Whitaker Foundation and the National Institutes of Health, grant numbers R01-HL62352-01 and P01-HL18208. The government may have certain rights in this invention.

FIELD OF THE INVENTION

The present invention relates to the preparation and use of vesicles and related encapsulating membranes made in aqueous solution from amphiphilic polymers and related molecules.

BACKGROUND OF THE INVENTION

Membranes that are stable in aqueous media are heavily relied upon for compartmentalization by biological cells. For instance, the outermost plasma membrane of a cell separates the inside of a cell from the outside and, like most cell membranes, it is a self-assembled, complex fluid of biological molecules, primarily lipids and proteins. Only a few molecules, such as water and small, uncharged organic molecules, significantly permeate the membrane. A biomembrane also possesses stability and other thermomechanical properties that are not unrelated to passive permeability and are certainly central to cell function (see, e.g., Lipowsky and Sackmann, Eds., *Structure and Dynamics of Membranes from Cells to Vesicles, Handbook of Biological Physics*, vol 1 (Elsevier Science, Amsterdam, 1995); Bloom et al., *Q. Rev. Biophys.* 24:293 (1991)).

The same characteristics of permeability and thermomechanical stability—in addition to biocompatibility—also affect how lipid vesicles that are assembled in vitro and that are also known as liposomes can effectively encapsulate and deliver a long list of bioactive agents (Needham et al., in *Vesicles*, M. Rosoff, Ed. (Dekker, New York, 1996), chap. 9; Cevc & Lasic in *Handbook of Biological Physics*, chaps. 9–10, 1995; Koltover et al., *Science* 281:78 (1998); Harasym et al., *Cancer Chemother. Pharmacol.* 40:309 (1997)). The typical liposome is comprised of one or more bilayer membranes, each approximately 5 nm thick and composed of amphiphiles such as phospholipids. Each bilayer exists as a temperature and solvent-dependent lamellar phase that is, in its surface, in a liquid, gel, or liquid-gel coexisting state. Because of a certain intrinsic biocompatibility of phospholipid vesicles, many groups have developed them for use as encapsulators and delivery vehicles. Vesicles surrounded by a lipid bilayer can range in diameter from as small as tens of nanometers to giants of 0.5–40 microns.

Phospholipid vesicles are materially weak and environmentally sensitive. Transit through the digestive tract, for example, can expose liposomes to a host of solubilizing agents. Repeated transit through the microcirculation can also tear apart giant phospholipid vesicles which cannot withstand high fluid shear. Smaller phospholipid vesicles may not fragment, but they tend to adhere, and are thus cleared from circulation. Circulating cells suppress their own adhesion partly through a brushy biopolymer layer, known as the glycocalyx, which faces the environment. The glycocalyx has, to some extent, been mimicked in liposome systems by the covalent addition to lipids of hydrophilic polyethyleneglycol (PEG) polymer chains. To maximally extend a vesicle's circulation lifetime (about ten hours), a suitable PEG weight ranges between about two and five kilograms/mole.

To further counteract mechanical forces imposed on their membranes, cells often also possess a sub-membranous network of cross-linked proteins (Alberts et al., in *Molecular Biology of the Cell*, $3^{rd}$ ed., pp489–493 and 800-1, Garland Publ., Inc., New York, 1999). The red blood cell, as an example, survives repeated deformation through the microcirculation without fragmentation, but only because it has a cross-linked network of peripheral membrane proteins. Without such a network, the cells cannot withstand such circulation for more than a few hours even with a glycocalyx (Schmid-Schoenbein et al, *Blut* 52(3):131 (1986)). With a normal membrane network, red blood cells circulate in humans for more than 100 days. In terms of measurable properties, the network imparts a shear elasticity that is only achievable with a cross-linked structure.

Past efforts to enhance the stability of lipid lamellae against shear and other factors, resulted in the synthesis of many different modified lipid molecules with polymerizable double bonds. Such bonds were located either at the surfactant head group, or more commonly, at different locations on the hydrophobic tails (Fendler et al., *Science* 223:888 (1984); Liu et al., *Macromolecules* 32:5519 (1996)). This approach clearly had the ability to generate covalently inter-connected poly-amphiphiles when reacted after self-assembly into membranes per ordinary lipids. However, a fully, covalently interconnected network of lipids requires complete cross-linking of the membrane of a vesicle, and the full extent of cross-linking achievable with cross-linkable lipids appears to be difficult to ascertain. O'Brien's group (Sisson et al., *Macromolecules* 29:8321 (1996)) has used solubility in hexafluoropropanol to estimate a degree of polymerization up to at least 1000. This corresponds to a vesicle diameter of about 10 nanometers, if one assumes complete cross-linking within and between layers of the bilayer, and a typical lipid area of about 0.5 square nanometers per lipid. Detergent induced leakage of entrapped solutes was strongly inhibited by cross-linking. It is clear, however, that no fully cross-linked lipid vesicle larger than several hundred nanometers has been reported.

A cross-linkable amphiphile related to cross-linkable phospholipids has been made by Komatsu et al., *J. Am. Chem. Soc.* 119:11660 (1997)). Tetrakis(aminophenyl)porphyrin contains four hydrophobic bixin side chains that each terminate in a small hydrophilic carboxylate group and harbor approximately ten (photo)reactive double bonds along the backbone of each bixin chain. When dissolved in the organic solvent, tetrahydrofuran (THF), and rapidly injected into a one-eighth volume of water and sonicated, the synthetic molecules reportedly formed vesicles. However, the resulting membranes are porous. Irradiation led to what was claimed to be the first spherical membrane structure of molecular thickness, which was considered a single, dehydratable, balloon-shaped polymer molecule insoluble in a predominantly organic solvent, such as 95% ethanol. Electron micrographs showed spherical particles of less than 100 nm, while collapsed particles studied by atomic force microscopy were reported to have a height of about 7 nm. Whether the cross-linked shells were truly semi-permeable vesicles or were highly porous macromolecular shells, as Komatsu et al. suggested, leaves open the question of whether, to date, a wholly cross-linked vesicle of any size has actually been produced. Certainly, no cross-linked vesicle larger than several hundred nanometers has been reported.

Small amphiphiles of natural origin, such as phospholipids have inspired the engineering of high molecular weight analogs, which also self-assemble into complex phases in aqueous media similar to those observed for phospholipids. For example, vesicles have been assembled in aqueous solution by Uchegbu et al., *J. Pharm. & Pharmacol.* 50:453 (1998)) using the naturally occurring macromolecule chitosan modified by the covalent attachment of many fatty acid pendant groups. The resulting self-assembled vesicles were 300–600 nanometers in diameter, and were shown to be bio- and haemocompatible. Although such modified natural products have disadvantages of variability in the natural polymer and a lack of precise control in covalent modification, the assembly of membranes from amphiphiles of high molecular weight has the potential to improve vesicle stability. The overall approach has similarities to lipid cross-linking, but a primary distinction lies in the fact that, with cross-linking, self-assembly of the membrane must occur first.

Many semi-orpartially synthetic, amphiphilic molecules are also significantly larger (in molecular weight, volume, and linear dimension) than phospholipid amphiphiles, and have therefore been called "super-amphiphiles" (Cornelissen et al., *Science* 280:1427 (1998)). Cornelissen et al. used polystyrene (PS) as a hydrophobic fraction in their series of non-synthetic, natural block copolymers designated PS40-b-(isocyano-L-alanine-L-alanine)y. For y=10, but not y=20 or 30, loop structures, referred to small collapsed vesicles, having diameters ranging from tens of nanometers to several hundred, and a bilayer thickness of 16 nanometer were mentioned as existing under a single acidic buffer condition (0.2 mM Na-acetate buffer, pH 5.6). However, bilayer filaments and superhelical rods existed, without explanation, under the same solution conditions, thus making the stability of the collapsed vesicles, relative to the other microstructures, highly uncertain for the studied dipeptide-base copolymer. Furthermore, no demonstration of semi-permeability was reported, and reasons for apparent vesicle collapse were not given, further raising questions of vesicle stability.

Additional spherical shell structures smaller than a few hundred nanometers, and which required the presence of organic solvents mixed into water to drive their formation, include those assembled from various block copolymers as observed by Yu et al., *Macromolecules* 31:1144(1998); Ding et al., *J. Phys. Chem. B* 102:6107(1998); Henselwood et al., *Macromolecules* 31:4213 (1998)). However, there appears in the prior art only one example of a wholly synthetic super-amphiphile that has the unpredicted capacity to self-assemble in aqueous solution, albeit only under moderately acidic pH conditions, into a vesicle-like microstructure, and that is the reported work of Cornelissen et al., 1998, although even those structures were of questionable state and stability.

Both amphiphiles and super-amphiphiles can exist in a broad variety of microphases and bulk phases that include not only lamellar, but also hexagonal, cubic, and more exotic phases (see review by Lipowsky and Sackmann, in *Handbook of Biological Physics*, 1995; Bates, *Science* 251:898 (1991). Based on the work of Hajduk et al. (see, *J. Phys. Chem. B* 102:4269 (1998)), the ability of super-amphiphilic block copolymers to form lamellar phases in aqueous solutions can be regulated by both synthetic tuning of polymer chemistry and physical variables, such as concentration and temperature. Evidence has now accumulated that in dilute solutions certain diblock copolymers, such as polyethyleneoxide-polyethylethylene (PEO—PEE, wherein PEO is structural equivalent to PEG), can form not only worm-like micelles (Won et al., *Science* 283:960-3 (1999)), but also unilamellar vesicles (Discher et al., *Science* 284:1143 (1999)).

In addition, because of the synthetic control over molecular composition, properties of membranes assembled from super-amphiphiles can be controlled in novel ways. For instance, a super-amphiphilic polymer can be made far more reactive than a much smaller phospholipid molecule simply because more reactive groups can be designed into the polymer. The principle was first illustrated for the aforementioned worm-like micelles in which polyethyleneoxide-polybutadiene (PEO—PBD) mesophases were successfully cross-linked into bulk materials with completely different properties, notably an enhanced shear elasticity (Won et al., 1999). The resulting microstructures, though assembled in water, could withstand dehydration, as well as exposure to an organic solvent, such as chloroform. In the absence of cross-linking, microstructures of amphiphiles and super-amphiphiles are generally unstable to treatments that could otherwise prove very useful for a range of applications that might benefit from, for example, sterilization, or long-term dry storage.

Despite recent advances, there remained until the present invention a long felt need in the art for stable, aqueous-formed vesicles which could be more broadly engineered but still have demonstrable features in common with a biomembrane or a mimic, including: biocompatibility, selective permeability to solutes, the ability to retain internal aqueous components and control their release, the ability to deform yet be relatively tough and resilient, and the ability to extensively cross-link within the membrane in order to withstand extreme environments.

SUMMARY OF THE INVENTION

The present invention meets the need in the art by providing not only an illustrative set of stable super-amphiphilic vesicles in biocompatible, aqueous solutions, but it also provides vesicles which are entirely synthetic, creating an opportunity to tailor the dynamics, structure, Theological and even optical responses of the membrane based on its composition. The polymer vesicles of the present invention are called "polymersomes." Analogous to "liposomes" made from phospholipids, the material properties of the polymersome vesicles can be readily measured using techniques that have been largely developed for phospholipid vesicles and biological cells. Furthermore, the ability to cross-link the polymer building blocks affords a novel opportunity to provide mechanical control and stability to the vesicle on the order of that which is provided by the protein skeleton at a cell's plasma membrane.

Polymersomes of the present invention possess membranes capable of self-repair, adaptability, portability, resilience, and are selectively permeable, thereby providing, for example, long-term, reliable and controllable vehicles for the delivery or storage of drugs or other compositions, such as oxygen, to the patient via the bloodstream, gastrointestinal tract, or other tissues, as replacement artificial tissue or soft biomaterial, as optical sensors, and as a structural basis for metal or alloy coatings to provide materials having unique electric or magnetic properties for use in high-dielectric or magnetic applications or as microcathodes.

In accordance with the present invention, there are provided vesicles comprising semi-permeable, thin-walled encapsulating membranes, wherein the membranes are formed in an aqueous solution, and wherein the membranes comprise one or more synthetic super-amphiphilic molecules. The invention relates to all super-amphiphilic molecules, which have hydrophilic block fractions within the range of 20–50% by weight, and which achieve some or all of the above capsular states of matter. Further provided are vesicles and encapsulating membranes, wherein at least one super-amphiphile molecule is a block copolymer, and wherein the resulting vesicle is termed a polymersome. The thus provided polymersomes may be comprised of multi-block copolymers, most preferably, but not limited to diblock or triblock copolymers. Moreover, in certain preferred embodiments of the present invention are provided polymersomes in which all of the super-amphiphile molecules are block copolymers. The block copolymers useful in the present invention may be selected from any known block copolymer, including, for example polyethylene oxide (PEO), poly(ethylethylene) (PEE), poly(butadiene) (PB or PBD), poly(styrene) (P S), and poly(isoprene) (PI). As needed, monomers for these polymers will be denoted by EO, EE, B or BD, S, and I, respectively.

In addition the present invention provides polymersomes, wherein the vesicles are capable of self-assembly in aqueous solution.

The present invention also provides methods for the preparation of mixtures of super-amphiphiles from smaller amphiphiles, such as phospholipids up to at least 20% mole fraction, which have also been shown capable of integrating into stable encapsulating membranes.

Further provided in the present invention are reactive amphiphiles that can be covalently cross-linked together, over a many micron-squared surface, while maintaining semi-permeability of the membrane. Cross-linked polymersome are characterized as having the ability to withstand exposure to organic solvents, boiling water, dehydration and rehydration in an aqueous solution without visibly or significantly affecting the integrity of the membrane.

In addition, the present invention provides polymersomes, wherein the vesicle is biocompatible. Further provided are vesicles for the retention, delivery, and/or extraction of materials, which may require membrane biocompatibility and may or may not take advantage of the novel thermal, mechanical, or chemical properties of the surrounding membranes.

The present invention also provides polymersomes which encapsulate one or more compositions, such as a drug, therapeutic compound, dye, nutrient, sugar, vitamin, protein or protein fragment, salt, electrolyte, gene or gene fragment, product of genetic engineering, steroid, adjuvant, biosealant, gas, ferrofluid, or liquid crystal. The polymersome may be further used to transport an encapsulatable material to or from its immediately surrounding environment.

Moreover, the present invention provides methods of using the polymersome or encapsulating membrane to transport one or more of the above identified compositions to or from a patient in need of such transport activity. For example, the polymersome could be used to deliver a drug or therapeutic composition to a patient's tissue or blood stream, or it could be used to remove a toxic composition from the blood stream of a patient with, for example, a life threatening hormone or enzyme imbalance.

Also provided by the present invention are methods of preparing a polymersome, wherein the preferred methods of preparation include at least one step consisting of a film rehydrating step, a bulk rehydrating step, or an electroforming step.

Further provided are methods for controlling the release of an encapsulated material from a polymersome by modulating and controlling the composition of the membrane. For example, one preferred method of controlling the release of an encapsulated material from a polymersome or encapsulating membrane entails cross-linking the membrane. In another preferred method, release of the encapsulated material is controlled by forming the encapsulating membrane from at least one cross-linkable amphiphile and at least one non cross-linkable molecule, followed by subjecting the thus destabilized membrane to chemical exposure or to waves of propagated light, sound, heat, or motion.

In addition, the present invention provides an encapsulating membrane comprising a semi-permeable, thin-walled encapsulating, amphiphilic membrane, wherein the membrane is formed around a droplet of oil in a microemulsion of oil dispersed in an aqueous solution, and wherein the membrane comprises one or more synthetic super-amphiphilic molecules. In a preferred embodiment, a super-amphiphile layer self-assembles around the oil droplet in water, with or without cross-linking of the super-amphiphile.

These and other aspects of the invention will become more apparent from the following detailed description when taken in conjunction with the following figures.

BRIEF DESCRIPTION OF THE FIGURES

FIG. 1A is a schematic representation of diblock copolymer $EO_{40}$-$EE_{37}$. The number-average molecular weight is~3900 g/mol. For a simple comparison of relative hydrophobic core thickness d, a typical lipid bilayer is schematically shown next to the assembly of copolymers. FIG. 1B depicts aqueous suspensions of $EO_{40}$-$EE_{37}$ vesicles in dominant co-existence with rod-like (black arrow) and spherical (gray arrow) micelles. Observations were made by cryo-TEM. The scale bar at lower left is 20 nm and the mean lamellar thickness is~8 nm with very little variation, consistent with unilamellar vesicles.

FIG. 2A depicts a vesicle immediately after electroformation in 100 mM sucrose solution. FIG. 2B depicts encapsulation of 10-kD Texas Red-labeled dextran. FIGS. 2C and 2D depict the microdeformation of a polymersome. The arrow marks the tip of an aspirated projection as it is pulled by negative pressure, $\Delta P$, into the micropipette. As shown, aspiration acts to (i) increase membrane tension, $\tau = \frac{1}{2}\Delta P R_p / (1 - R_p/R_s)$, where micropipette $R_p$ and $R_s$ are the respective radii of the micropipette and the outer spherical contour; and (ii) expand the original, projected vesicle surface area, $A_o$, by the increment $\Delta A$.

FIG. 3A shows membrane elasticity in terms of membrane tension versus area expansion. Filled circles indicate aspiration; open circles indicate graded release. The upper left inset shows the distribution of measurements for the bending modulus, $K_b$, as obtained from the initial phase of aspiration. The lower right inset shows the distribution of measurements for the area expansion modulus, $K_a$, as obtained from the linear phase of aspiration. FIG. 3B shows membrane toughness as determined by aspiration to the point of rupture (asterisk). For comparison, aspiration to the point of rupture of an electroformed 1-stearoyl-2oleoyl phosphatidylcholine (SOPC) lipid vesicle is also shown.

FIG. 5A shows the membrane's area expansion with increasing temperature, and its stability at 37° C. The vesicle is held at a fixed membrane tension of less than 4 mN/m. Relative polymer vesicle area, $\alpha$, is shown against temperature. The overall thermal expansivity is approximately $1.9 \times 10^{-3}$ per degree C. FIG. 5B demonstrates the long-term stability of polymersomes in phosphate buffered saline (PBS).

FIG. 6A shows the uniformity of fluorescence (3 mol %) around an aspirated contour of membrane. The radius of the pipette is about 2.5 microns. FIG. 6B shows that the contour intensity increases linearly up to about 10 mol % Texas Red PE.

FIG. 7A shows a 15 μm polymersome encapsulating myoglobin. FIG. 7B shows a 5 μm polymersome encapsulating hemoglobin. FIGS. 7C and 7D show a 25 μm polymer vesicle containing fluorescein-tagged bovine serum albumin (BSA) encapsulated at 0.5 g/l 24 hours earlier and viewed in phase contrast (FIG. 7C) and fluorescence (FIG. 7D), respectively.

FIGS. 8B and 8C depict the complete lack of activation of the white cell (which would be observed as extension of pseudopods) or adhesion between the cells at time points 62 and 63 seconds, respectively, after initial contact.

FIG. 9B depicts a fluid phase vesicle, which has been osmotically deflated, resulting in a flaccid shape, but maintaining a smooth contour. By comparison, FIG. 9D depicts a solid-like, cross-linked membrane, which has been osmotically deflated, resulting in a flaccid shape which is not smooth.

FIG. 10A depicts a vesicle in aqueous solution being pulled into a micropipette ($R_p$=4.5 μm) by negative pressure, $\Delta P$. FIG. 10B depicts the same vesicle imaged immediately after being placed into chloroform. No noticeable change was observed in the vesicle after 30 minutes exposure to the chloroform (FIG. 1C), nor after return of the vesicle back into the aqueous solution (FIG. 10D).

FIG. 1 depicts the dehydration of a vesicle upon exposure to air.

FIG. 12A is the micropipette aspiration curve for a single, initially flaccid and smooth contour vesicle pulled to a length L into a micropipette. $R_p$ is the micropipette radius. At high aspiration pressures, the vesicle interior becomes hydrostatically pressurized. The reversible, initial slope of such a curve is plotted, for a total of ten vesicles, against $R_{ves}/R_p$ in FIG. 12B. This initial slope vanishes in the limit of $R_{ves}$=$R_p$, and, above this, resistance to aspiration increases linearly with $R_{ves}/R_p$. The slope of the fitted line provides an estimate of the membrane's elastic shear modulus ($\mu$) which is independent of vesicle size and which is a property arising only with cross-linking.

FIG. 13A depicts amphiphilic PEO—PBD copolymers, self-assembled at the oil-water interface of oil droplets in water (micro-emulsion), with PEO facing the water and PBD facing the oil. The cross-linking lines represent the new bonds formed due to exposure of PBD to free radicals. As shown in FIG. 13B, the covalently cross-linked PBD layer makes the emulsion so stable, that the oil droplets can be aspirated into a micropipette ($R_p$=4 μm) without fragmentation.

FIG. 14A shows 60:40 $EO_{26}$-$BD_{46}$:$EO_{40}$-$EE_{37}$ vesicle after the cross-linking reaction was completed. FIGS. 14B and 14C show the same vesicle aspirated into a micropipette ($R_p$=1.5 μm) by negative pressure, $\Delta P$=2 cm of water, and $\Delta P$=10 cm of water, respectively. The increased pressure in FIG. 14C leads to perforation of the membrane and leakage of its contents.

DETAILED DESCRIPTION OF THE INVENTION

Figure 1:
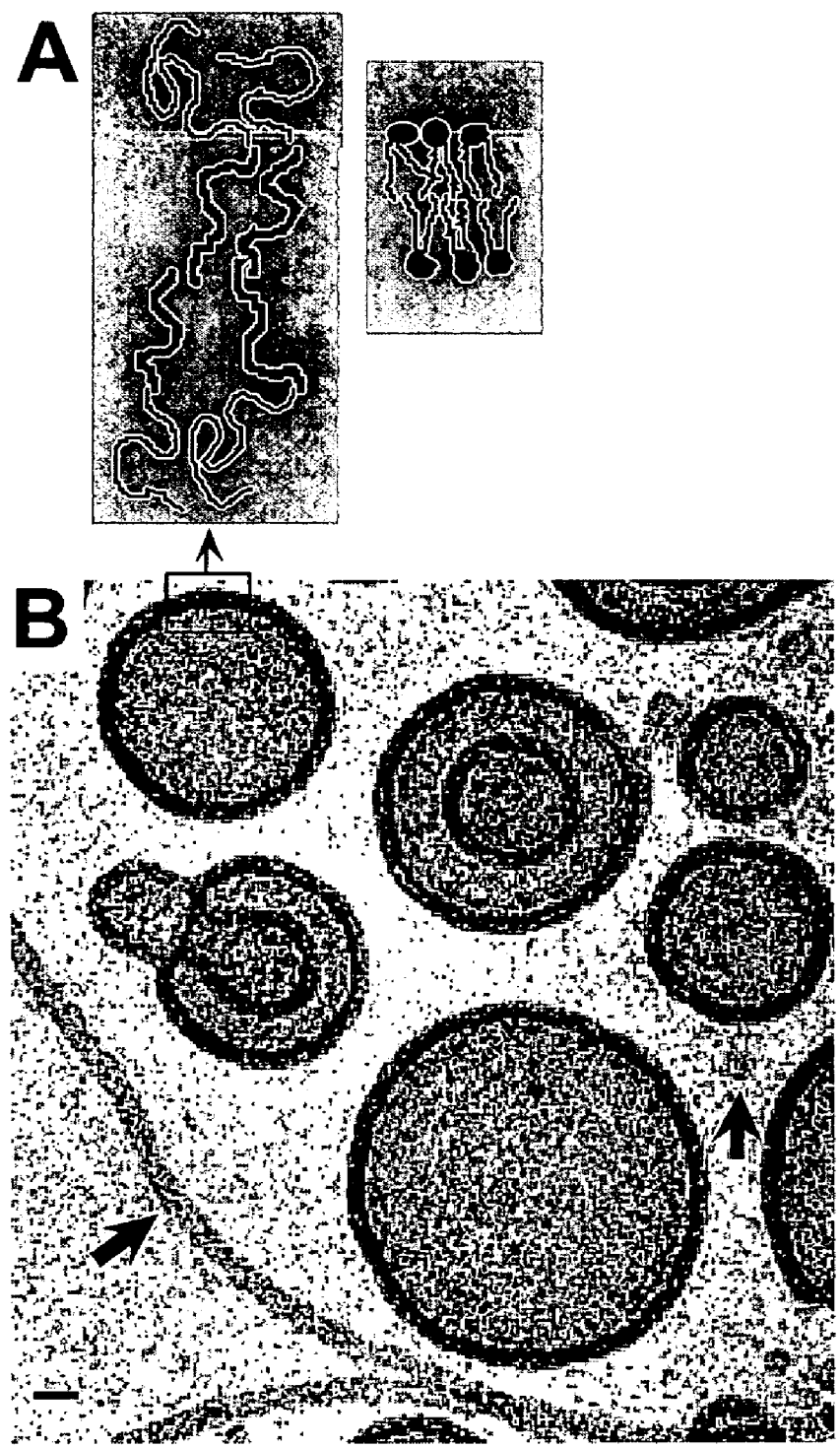
FIG. 1 depicts the molecular assemblies and copolymer structures in water.

The present invention provides stable vesicles comprising, semi-permeable, thin-walled encapsulating membranes, tens of nanometers to tens of microns in diameter, made by self-assembly in various aqueous solutions of purely synthetic, amphiphilic molecules having an average molecular weight of many kilograms per mole. Such molecules are referred to as "super-amphiphiles" because of their large molecular weight in comparison to other amphiphiles, such as the phospholipids and cholesterol of eukaryotic cell membranes.

The relevant class of super-amphiphilic molecules is represented by, but not limited to, block copolymers, e.g., hydrophilic polyethyleneoxide (EO) linked to hydrophobic polyethylethylene (EE). The synthetic diversity of block copolymers provides the opportunity to make a wide variety of vesicles with material properties that greatly expand what is currently available from the spectrum of naturally occurring phospholipids. For the purposes of this invention, although technically distinct and distinguished on the basis of molecular weight, the terms "super-amphiphile" and "amphiphile" are used interchangeably, for example, to refer to the block copolymers of the present invention.

In a preferred embodiment, the invention further provides for the preparation of vesicles harboring mixtures of super-amphiphiles and smaller amphiphiles, such as phospholipids up to at least 20% mole fraction. The latter have been shown to be capable of integrating into stable vesicles of super-amphiphiles.

"Vesicles," as the term is used in the present invention, are essentially semi-permeable bags of aqueous solution as surrounded (without edges) by a self-assembled, stable membrane composed predominantly, by mass, of either amphiphiles or super-amphiphiles which self-assemble in water or aqueous solution. Thus, a biological cell would, in general, represent a naturally occurring vesicle. Smaller vesicles are also found within biological cells, and many of the structures within a cell are vesicular. The membrane of an internal vesicle serves the same purpose as the plasma membrane, i.e., to maintain a difference in composition and an osmotic balance between the interior of the vesicle and the exterior. Many additional functions of cell membranes, such as in providing a two-dimensional scaffold for energy conversion can be added to compartmentalization roles. For an intracellular vesicle, the environment outside the vesicle is the cytoplasm.

The "cell membrane" or "plasma membrane" is a complex, contiguous, self-assembled, complex fluid structure comprised of amphiphilic lipids in a bilayer with associated proteins and which defines the boundary of every cell. It is also referred to as a "biomembrane." "Phospholipids" comprise lipid substances, which occur in cellular membranes and contain esters of phosphoric acid, such as sphingomyelins, and include phosphatides, phospholipins and phospholipoids.

Synthetic amphiphiles having molecular weights less than a few kilodaltons, like natural amphiphiles, are pervasive as self-assembled, encapsulating membranes in water-based systems. These include complex fluids, soaps, lubricants, microemulsions consisting of oil droplets in water, as well as biomedical devices such as vesicles. An "encapsulating membrane," as the term is used in the present invention, is a vesicle in all respects except for the necessity of aqueous solution. Encapsulating membranes, by definition, compartmentalize by being semi- or selectively permeable to solutes, either contained inside or maintained outside of the spatial volume delimited by the membrane. Thus, a vesicle is a capsule in aqueous solution, which also contains aqueous solution. However, the interior or exterior of the capsule could also be another fluid, such as an oil or a gas. A "capsule," as the term is used in the present invention, is the encapsulating membrane plus the space enclosed within the membrane.

"Complex fluids" are fluids that are made from molecules that interact and self-associate, conferring novel Theological, optical, or mechanical properties on the fluid itself. Complex fluids are found throughout biological and chemical systems, and include materials such as biological membranes or biomembranes, polymer melts and blends, and liquid crystals. The self-association and ordering of the molecules within the fluid depends on the interaction between component parts of the molecules, relative to their interaction with solvent, if present.

The plasma membrane is a "lipid bilayer" comprising a double layer of phospholipid/diacyl chains, wherein the hydrophobic fatty acid tails of the phospholipids face each other and the hydrophilic polar heads of each layer face outward toward the aqueous solutions (see FIG. 1A). Numerous receptors, steroids, transporters and the like are embedded within the bilayer of a typical cell. Thus, a "lipid vesicle" or "liposome," is a vesicle surrounded by a membrane comprising one or more phospholipids. Throughout the specification the terms "cell membrane," "plasma membrane," "lipid membrane," and "biomembrane" may be used interchangeably to refer to the same lipid bilayer surrounding a cell or vesicle.

A "membrane", as the term is used in this invention, is a spatially distinct collection of molecules that defines a 2-dimensional surface in 3-dimensional space, and thus separates one space from another in at least a local sense. Such a membrane must also be semi-permeable to solutes. It must also be sub-microscopic (less than optical wavelengths of around 500 nm) in its thickness (d in FIG. 1A), as resulting from a process of self-assembly. It can have fluid or solid properties, depending on temperature and on the chemistry of the amphiphiles from which it is formed. At some temperatures, the membrane can be fluid (having a measurable viscosity), or it can be solid-like, with an elasticity and bending rigidity. The membrane can store energy through its mechanical deformation, or it can store electrical energy by maintaining a transmembrane potential. Under some conditions, membranes can adhere to each other and coalesce (fuse). Soluble amphiphiles can bind to, and intercalate within a membrane.

A "bilayer membrane" (or simply "bilayer(s)") for the purposes of this invention is a self assembled membrane of amphiphiles or super-amphiphiles in aqueous solutions.

"Polymersomes" are vesicles, which are assembled from synthetic polymers in aqueous solutions. Unlike liposomes, a polymersome does not include lipids or phospholipids as its majority component. Consequently, polymersomes can be thermally, mechanically, and chemically distinct and, in particular, more durable and resilient than the most stable of lipid vesicles. The polymersomes assemble during processes of lamellar swelling, e.g., by film or bulk rehydration or through an additional phoresis step, as described below, or by other known methods. Like liposomes, polymersomes form by "self assembly," a spontaneous, entropy-driven process of preparing a closed semi-permeable membrane.

Because of the bilayer's perselectivity, materials may be "encapsulated" in the aqueous interior or intercalated into the hydrophobic membrane core of the polymersome vesicle of the present invention. Numerous technologies can be developed from such vesicles, owing to the numerous unique features of the bilayer membrane and the broad availability of super-amphiphiles, such as block copolymers.

The synthetic polymersome membrane can exchange material with the "bulk," i.e., the solution surrounding the vesicles. Each component in the bulk has a partition coefficient, meaning it has a certain probability of staying in the bulk, as well as a probability of remaining in the membrane. Conditions can be predetermined so that the partition coefficient of a selected type of molecule will be much higher within a vesicle's membrane, thereby permitting the polymersome to decrease the concentration of a molecule, such as cholesterol, in the bulk. In a preferred embodiment, phospholipid molecules have been shown to incorporate within polymersome membranes by the simple addition of the phospholipid molecules to the bulk. In the alternative, polymersomes can be formed with a selected molecule, such as a hormone, incorporated within the membrane, so that by controlling the partition coefficient, the molecule will be released into the bulk when the polymersome arrives at a destination having a higher partition coefficient.

The polymersomes of the present invention are formed from synthetic, amphiphilic copolymers. An "amphiphilic" substance is one containing both polar (water-soluble) and hydrophobic (water-insoluble) groups. "Polymers" are macromolecules comprising connected monomeric units. The monomeric units may be of a single type (homogeneous), or a variety of types (heterogeneous). The physical behavior of the polymer is dictated by several features, including the total molecular weight, the composition of the polymer (e.g., the relative concentrations of different monomers), the chemical identity of each monomeric unit and its interaction with a solvent, and the architecture of the polymer (whether it is single chain or branched chains). For example, in polyethylene glycol (PEG), which is a polymer of ethylene oxide (EO), the chain lengths which, when covalently attached to a phospholipid, optimize the circulation life of a liposome, is known to be in the approximate range of 34–114 covalently linked monomers ($EO_{34}$ to $EO_{114}$).

The preferred class of polymer selected to prepare the polymersomes of the present invention is the "block copolymer." Block copolymers are polymers having at least two, tandem, interconnected regions of differing chemistry. Each region comprises a repeating sequence of monomers. Thus, a "diblock copolymer" comprises two such connected regions (A-B); a "triblock copolymer," three (A-B-C), etc. Each region may have its own chemical identity and preferences for solvent. Thus, an enormous spectrum of block chemistries is theoretically possible, limited only by the acumen of the synthetic chemist.

In the "melt" (pure polymer), a diblock copolymer may form complex structures as dictated by the interaction between the chemical identities in each segment and the molecular weight. The interaction between chemical groups in each block is given by the mixing parameter or Flory interaction parameter, $\chi$, which provides a measure of the energetic cost of placing a monomer of A next to a monomer of B. Generally, the segregation of polymers into different ordered structures in the melt is controlled by the magnitude of $\chi N$, where N is proportional to molecular weight. For example, the tendency to form lamellar phases with block copolymers in the melt increases as $\chi N$ increases above a threshold value of approximately 10.

A linear diblock copolymer of the form A-B can form a variety of different structures. In either pure solution (the melt) or diluted into a solvent, the relative preferences of the A and B blocks for each other, as well as the solvent (if present) will dictate the ordering of the polymer material. In the melt, numerous structural phases have been seen for simple AB diblock copolymers.

To form a stable membrane in water, the absolute minimum requisite molecular weight for an amphiphile must exceed that of methanol $HOCH_3$, which is undoubtedly the smallest canonical amphiphile, with one end polar (HO—) and the other end hydrophobic (—$CH_3$). Formation of a stable lamellar phase more precisely requires an amphiphile with a hydrophilic group whose projected area, when viewed along the membrane's normal, is approximately equal to the volume divided by the maximum dimension of the hydrophobic portion of the amphiphile (Israelachvili, in *Intermolecular and Surface Forces*, $2^{nd}$ ed., Pt3 (Academic Press, New York) 1995).

The most common lamellae-forming amphiphiles also have a hydrophilic volume fraction between 20 and 50%. Such molecules form, in aqueous solutions, bilayer membranes with hydrophobic cores never more than a few nanometers in thickness. The present invention relates to all super-amphiphilic molecules which have hydrophilic block fractions within the range of 20–50% by volume and which can achieve a capsular state. The ability of amphiphilic and super-amphiphilic molecules to self-assemble can be largely assessed, without undue experimentation, by suspending the synthetic super-amphiphile in aqueous solution and looking for lamellar and vesicular structures as judged by simple observation under any basic optical microscope or through the scattering of light.

For typical phospholipids with two acyl chains, temperature can affect the stability of the thin lamellar structures, in part, by determining the volume of the hydrophobic portion. In addition, the strength of the hydrophobic interaction, which drives self-assembly and is required to maintain membrane stability, is generally recognized as rapidly decreasing for temperatures above approximately 50° C. Such vesicles generally are not able to retain their contents for any significant length of time under conditions of boiling water.

Upper limits on the molecular weight of synthetic amphiphiles which form single component, encapsulating membranes clearly exceed the many kilodalton range, as concluded from the work of Discher et al., (1999), which contributes foundationally to the present invention, and is herein incorporated by reference.

Block copolymers with molecular weights ranging from about 2 to 10 kilograms per mole can be synthesized and made into vesicles when the hydrophobic volume fraction is between about 20% and 50%. Diblocks containing polybutadiene are prepared, for example, from the polymerization of butadiene in cyclohexane at 40° C. using sec-butyllithium as the initiator. Microstructure can be adjusted through the use of various polar modifiers. For example, pure cyclohexane yields 93% 1.4 and 7% 1.2 addition, while the addition of THF (50 parts per Li) leads to 90% 1.2 repeat units. The reaction may be terminated with, for example, ethyleneoxide, which does not propagate with a lithium counterion and HCl, leading to a monofunctional alcohol. This PB—OH intermediate, when hydrogenated over a palladium (Pd) support catalyst, produces PEE-OH. Reduction of this species with potassium naphthalide, followed by the subsequent addition of a measured quantity of ethylene oxide, results in the PEO—PEE diblock copolymer. Many variations on this method, as well as alternative methods of synthesis of diblock copolymers are known in the art; however, this particular preferred method is provided by example, and one of ordinary skill in the art would be able to prepare any selected diblock copolymer.

For example, if PB—PEO diblock copolymers were selected, the synthesis of PB—PEO differs from the previous scheme by a single step, as would be understood by the practitioner. The step by which PB—OH is hydrogenated over palladium to form PEO—OH is omitted. Instead, the PB—OH intermediate is prepared, then it is reduced, for example, using potassium naphthalide, and converted to PB—PEO by the subsequent addition of ethylene oxide.

In yet another example, triblock copolymers having a PEO end group can also form polymersomes using similar techniques. Various combinations are possible comprising, e.g., polyethylene, polyethylethylene, polystyrene, polybutadiene, and the like. For example, a polystyrene (PS)—PB—PEO polymer can be prepared by the sequential addition of styrene and butadiene in cyclohexane with hydroxyl functionalization, re-initiation and polymerization. PB—PEE-PEO results from the two-step polymerization of butadiene, first in cyclohexane, then in the presence of THF, hydrolyl functionalization, selective catalytic hydrogenation of the 1.2PB units, and the addition of the PEO block.

A plethora of molecular variables can be altered with these illustrative polymers, hence a wide variety of material properties are available for the preparation of the polymersomes. ABC triblocks can range from molecular weights of 3,000 to at least 30,000 g/mol. Hydrophilic compositions should range from 20–50% in volume fraction, which will favor vesicle formation. The molecular weights must be high enough to ensure hydrophobic block segregation to the membrane core. The Flory interaction parameter between water and the chosen hydrophobic block should be high enough to ensure said segregation. Symmetry can range from symmetric ABC triblock copolymers (where A and C are of the same molecular weight) to highly asymmetric triblock copolymers (where, for example, the C block is small, and the A and B blocks are of equal length).

TABLE 1 lists some of the synthetic super-amphiphiles of many kilograms per mole in molecular weight, which are capable of self-assembling into semi-permeable vesicles in aqueous solution. The panel of preferred PEO—PEE block copolymers ranges in molecular weight from 1400 to 8700, with hydrophilic volume fraction, $f_{EO}$, ranging from 20% to 50%. The polydispersity indices for the resulting polymers do not exceed 1.2, confirming a narrow polydispersity.

TABLE 1

| Super-Amphiphile* | Molecular Weight (g/mol)** | Vol. fraction EO (±1%)† |
|---|---|---|
| $EO_{40}$-$EE_{37}$ | 3900 | 39% |
| $EO_{43}$-$EE_{35}$ | 3900 | 42% |
| $EO_{49}$-$EE_{37}$ | 4300 | 44% |
| $EO_{26}$-$PB_{46}$ | 3600 | 28% |
| $EO_{31}$-$PB_{46}$ | 3800 | 31% |
| $EO_{42}$-$PB_{46}$ | 5300 | 37% |
| $EO_{33}$-$S_{10}$-$I_{22}$‡‡ | 3900 | 33% |
| $EO_{48}$-$EE_{75}$-$EO_{48}$ | 8400 | 44% |

*EO = ethyleneoxide, EE = ethylethylene, B = butadiene, S = styrene, I = isoprene
**Molecular Weight denotes number-average molecular weight (Mn) ± 50 g/mol
†Volume fractions determined by NMR.
‡‡EO-S-I has number-average molecular weight for the respective blocks of 1440, 1008, 1470 g/mol.

TABLE 1 is intended only to be representative of the synthetic super-amphiphiles suitable for use in the present invention. It is not intended to be limiting. The table can be effectively used to select which block copolymers will form lamellar phases and vesicles. One of ordinary skill in the art will readily recognize many other suitable block copolymers that can be used in the preparation of polymersomes based on the teachings of the present invention.

In a preferred embodiment of the present invention, polymersomes comprise the selected polymer polyethyleneoxide-polyethylethylene ($EO_{40}$-$EE_{37}$), also designated OE-7, and having a chain structure t-butyl-$[CH_2$—$CH(C_2H_5)]_{37}$—$[CH_2$—$CH_2$—$O]_{40}$—H. The molecule's average molecular weight is about five to ten times greater than that of typical phospholipids in natural membranes. The resulting polymersome membrane is found to be at least 10 times less permeable to water than common phospholipid bilayers.

Figure 4:
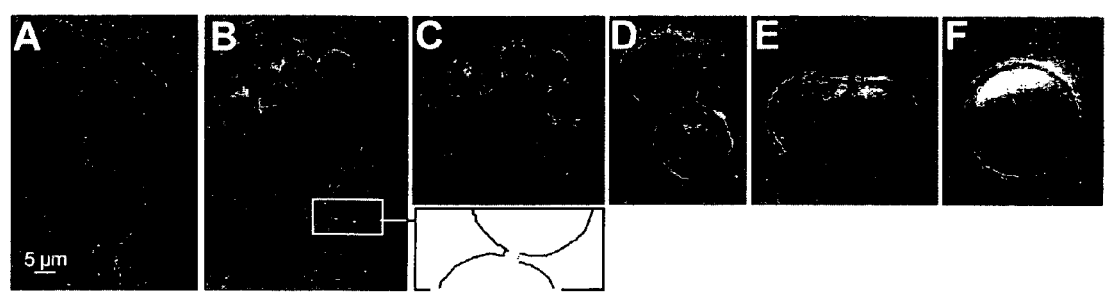
FIG. 4 depicts shape transformations driven by osmotic swelling of a single polymersome as imaged by phase contrast video microscopy. The vesicle was formed in 100 mOsm sucrose, and the external sucrose solution was progressively diluted with distilled water from~150 mOsm glucose over a period of 90 min. The transformation is shown as a progression beginning with FIG. 4A, which shows a giant tubular state that swells with the initial appearance of interconnected spheres that conserve vesicle topology, shown in FIGS. 4B through 4C and inset. This is followed by the coalescence and disappearance of the small spheres, a form of Ostwald ripening (FIGS. 4D through 4E) before final transformation to a single, tensed sphere (FIG. 4F). The entire swelling sequence is predicated on the vesicle's non-zero permeability to water accompanied by impermeability to the entrapped sucrose solute.

A vesicle suspended in water which encapsulates impermeable solutes and which has a non-zero membrane permeability to water can be osmotically forced to change its shape. Shape transformations of vesicle capsules, the simple red blood cell included, have generally been correlated with energy costs or constraints imposed by vesicle area, the number of membrane molecules making up the vesicle area, the volume enclosed by the vesicle, and the curvature elasticity of the membrane (see, e.g., Deuling et al., *J. Phys.* 37:1335 (1976); Svetina et al., *Eur. Biophys.* 17:101 (1989); Seifert et al., *Phys. Rev. A* 44:1182 (1991)). Theoretical and experimental efforts on fluid lipid bilayers (e.g., Seifert and Lipowsky, in *Handbook of Biological Physics*, chap. 8; Dobereiner et al., *Phys. Rev. E* 55:4458 (1997)) have separated the elasticity in bending between a local, $K_b$-scaled curvature energy term that includes a spontaneous curvature, $c_o$, and a more non-local, area-difference-elasticity term predicated on monolayer unconnectedness in spherical-topology vesicles. To oppose any relaxation of leaflet area difference, a lack of lipid transfer or "flip-flop" between layers must be postulated. Only with such a non-local area difference term can a vesicle maintain in apparent equilibrium the type of multi-sphere and budded morphologies observable in both lipid systems (Chaieb et al., *Phys. Rev. E* 58:7733 (1998)) and in the osmotically deflated polymersomes shown in FIG. 4. Because worm-like and spherical micelles are also in evidence (FIG. 1B), however, a non-zero $c_o$ also appears likely. Heterogeneity in the morphology of polymersomes, both small (FIG. 1B) and large vesicles (FIG. 4), denotes, however, an important contribution from monolayer area difference, a process-dependent feature that arises upon vesicle closure.

Figure 2:
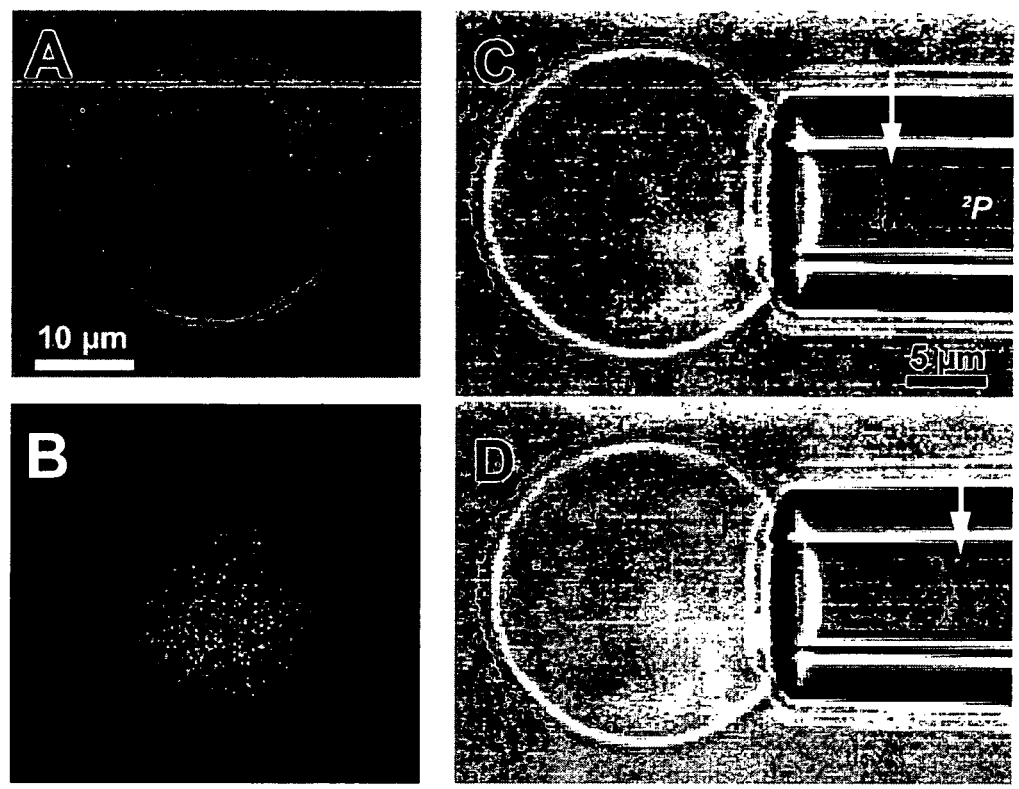
FIG. 2 depicts giant unilamellar vesicles of $EO_{40}$-$EE_{37}$.

The tool that has been used to measure many of the material properties of bilayer vesicles is "micropipette aspiration" as applied in FIG. 2. In micropipette aspiration, the rheology and material properties of micron-sized objects are measured using glass pipettes. Small, micron diameter pipettes are used to pick up, deform and manipulate micron-sized objects, such as giant lipid vesicles. The aspiration pressure is controlled by manometers, in which the hydrostatic pressure in a reservoir connected to the micropipette is varied in relation to a fixed reference. Pressure may be varied with a resolution of microns of $H_2O$ (or $10^{-6}$ atm).

A deformable object is aspirated using a pressure driving force (or suction pressure), $\Delta P$, and the object is drawn within the pipette to a projection length $L_p$. For a liquid, the tension in the membrane, $\tau$, can be obtained from the Law of Laplace in terms of the pressure driving force, the pipette inner radius, $R_P$, the vesicular outer diameter, $R_S$, and the length of the projection. This technique has been used to measure the moduli of deformation and strength of lipid vesicle membranes, such as the bending modulus ($K_b$), the area expansion modulus ($K_a$), the critical areal strain to the point of failure ($\alpha_c$) and the toughness ($E_c$ or $T_f$) (the energy stored in the vesicle prior to failure) (see, e.g., Evans et al., *J. Phys. Chem.* 91:4219 (1987); Needham et al., *Biophys. J.* 58:997 (1990)). The bending modulus is measured by exerting small tensions on the membrane, to smooth out thermally-driven surface undulations. At larger tensions, beyond a crossover tension at which the undulations of the membrane have been smoothed, the tension acts to stretch the membrane in-plane against the cohesive hydrophobic forces holding the membrane together. The area expansion modulus is the unit tension required for a unit increase in strain. The critical area strain is obtained by stressing the membrane to the point of cohesive failure. Thus, micropipette aspiration is a powerful tool for exploring the interfacial and material properties of the polymersomes of the present invention.

TABLE 2 demonstrates that the membrane mechanical properties of several preferred polymer vesicles are independent of the different methods of assembly in aqueous media $K_a$ falls within the broad range of lipid membrane measurements. In contrast, the giant polymersomes of the present invention prove to be almost an order of magnitude tougher and sustain far greater areal strain under tension before rupture than any naturally occurring or synthetic vesicle known in the art. Membranes formed from the preferred super-amphiphilic diblocks of either polyethyleneoxide-polyethylethylene or polyethyleneoxide-polybutadiene have also been shown to be thicker than lipid membranes, providing a physical basis for understanding the enhanced toughness, as well as the reduced permeability.

be so limited. Nevertheless, use of the Bates method results in very low polydispersity indices for the synthesized polymer (not exceeding 1.2), and make the methods particularly suited for use in the present invention, at least from the standpoint of homogeneity. Indeed, the demonstrated ability to make stable vesicles from PEO—PEE with up to at least 20% mole fraction of phospholipid strongly indicates that polydispersity need not be limiting in the formation of stable vesicles.

Vesicles can be prepared by any method known to one of ordinary skill in the art. However, the preferred method of

TABLE 2

| Super-Amphiphile | Method of Formation | $K_a$ (mN/m)* | $\alpha_c = (\Delta A/Ao)$** | d: thickness*** |
|---|---|---|---|---|
| $EO_{40}$-$EE_{37}$ | Film Rehydration | 115 ± 27 [20 vesicles] | 0.20 ± 0.07 [5 vesicles] | 8 ± 1 nm |
|  | Electroformation | 120 ± 20 [21 vesicles] | 0.19 ± 0.02 [6 vesicles] |  |
| $EO_{26}$-$B_{46}$ | Film Rehydration | 80 ± 34 [5 vesicles] |  | 9 ± 1 nm |
|  | Bulk Rehydration | 94 ± 10 [4 vesicles] |  |  |
| $EO_{50}$-$B_{54}$ | Film Rehydration | 82 ± 23 [9 vesicles] | 0.30 [2 vesicles] |  |

*$K_a$ is the elastic modulus for area expansion.
**$\alpha_c$ is the critical area strain at which an initially unstressed membrane will rupture.
***The hydrophobic core thickness, d, is determined by electron microscopy.

Preferred assemblies of the present invention can withstand exceptionally severe environmental conditions of temperature and exposure to solvent. TABLE 3 indicates the result of suspending vesicles of $EO_{40}$-$EE_{37}$ in a sterilizing aqueous solution of ethanol in phosphate buffered saline (PBS) for at least 15 minutes. Many phospholipid vesicles would be unstable under such solvent conditions.

TABLE 3

|  | 25% EtOH in PBS | PBS |
|---|---|---|
| Vesicle per ml* | $7.2 \times 10^4$ | $9.0 \times 10^4$ |
| Vesicle diameter (μm) | 9.7 ± 5.4 | 8.6 ± 4.1 |

*5 μl of vesicles in 247 mOsm sucrose were added to 200 μl of 25% EtOH/PBS or PBS.

The methods and examples that follow make use of and extend the above characterization methods and concepts.

A. Preparation of Polymersomes

In the preferred embodiments of the present invention, the polymersomes are comprised of a subset class of block copolymers—the "amphiphilic block copolymers," meaning that in a diblock copolymer, region A is hydrophilic and region B is hydrophobic. Like phospholipid amphiphiles, block copolymer amphiphiles self-assemble into lamellar phases at certain compositions and temperatures and can form closed bilayer structures capable of encapsulating aqueous materials. Vesicles from block-copolymer amphiphiles have the additional advantage of being made from synthetic molecules, permitting one of ordinary skill to apply known synthetic methods to greatly expand the types of vesicles and the material properties that are possible based upon the presently disclosed and exemplified applications.

The diblock copolymers used to form the super-amphiphile vesicles of the invention may be synthesized by any method known to one of ordinary skill in the art for synthesizing copolymers. Such methods are taught, for example, by Hajduk et al., 1998; Hillmyer and Bates, *Macromolecules* 29, 6994 (1996); and Hillmyer et al., *Science* 271:976 (1996)), although the practitioner need not preparation is film rehydration, which has yielded vesicles for all copolymers that have been found to be capable of forming vesicles. Other methods can be used as described below, but they do not guarantee vesicle formation for all "vesicle-forming" amphiphiles.

(1) Film Rehydration

In the film rehydration method, in general, pure amphiphiles are dissolved in any suitable solvent that can be completely evaporated without distracting the amphiphile, at concentrations preferably ranging from 0.1 to 50 mg/ml, more preferably from 1 to 10 mg/ml, most preferably yielding 1 μmol/ml solution. The preferred solvent for this purpose in the present invention is chloroform. When amphiphile mixtures are used, each component of the mixture must be dissolved separately and mixed in a measured aliquot of the solvent to obtain a solution comprising the desired ratio of components. The resulting solution is placed into a glass vial, and the solvent is evaporated to yield a thin film, having a preferable density of approximately 0.01 μmol/cm².

When chloroform is used as the solvent, the solution is evaporated under nitrogen gas and under applied vacuum for three hours or longer, until evaporation is completed. After complete evaporation of the solvent, an aqueous solution comprising the "to be encapsulated" material is added to the glass vial, yielding a preferred 0.1% (w/w) solution. Vesicles form spontaneously at room temperature in a time dependent manner ranging from several hours to several days, depending on the selected amphiphile and the aqueous solvent and the ratio between them. Temperature may be used as a control variable in this process of formation. The yield of vesicles can be optimized without undue experimentation by the selection of aqueous components and by tuning the experimental conditions, such as concentration and temperature.

(2) Bulk Rehydration

In the alternative, the pure amphiphile can be mixed with an aqueous solution to a preferred concentration of 0.01–1% (w/w), most preferably 0.1% (w/w), then dissolved into small aggregates (with dimensions of several microns) by mixing. When the aggregates are then incubated without any perturbance for several hours to several days, depending on the amphiphile, aqueous solvent and temperature, vesicles form spontaneously on the aggregate surface, from which they can be dissociated by gentle mixing or shaking.

(3) Electroformation

Polymersomes are more preferably made by electroformation, by using the adapted methods of Angelova et al., *Prog. Coll. Polym. Sci.* 89:127 (1992), which have been previously used by Hammer as reported by Longo et al., *Biophys. J.* 73:1430 (1997) (both are herein incorporated by reference), although the preparation need not be so limited. Briefly, by example, 20 µl of the amphiphile solution (in chloroform or other solvent made to preferable concentration 1 µmol/ml) is deposited as a film on two 1 mm-diameter adjacent platinum wire electrodes held in a Teflon frame (5 mm separation of the electrodes). The solvent is then evaporated under nitrogen, followed by vacuum drying for 3 to 48 hours. The Teflon frame and coated electrodes are then assembled into a chamber, which is then sealed with coverslips. Preferably, the temperature and humidity of the chamber are controlled. The chamber is subsequently filled with a degassed aqueous solution, e.g., glucose or sucrose, preferably about 0.1 to 0.25 M or with a protein solution containing, for example, a globin.

To begin generating polymersomes from the film, an alternating electric field is applied to the electrodes (e.g., 10 Hz, 10 V) while the chamber is mounted and viewed on the stage of an inverted microscope. Giant vesicles attached to the film-coated electrode are visible after 1 to 60 min. The vesicles can be dissociated from the electrodes by lowering the frequency to about 3 to 5 Hz for at least 15 min, and by removing the solution from the chamber into a syringe.

In spite of several techniques used, it was found in practicing the present invention, that for each of the particular amphiphiles studied, the method selected for vesicle formation did not alter the mechanical properties of the resulting vesicles (TABLE 2).

(4) Fragmentation

The size of giant polymersome can be decreased to any average vesicle size as desired for a given application by filtration through polycarbonate filter (Osmonics, Livermore, Calif.). As an example, 5.5±3.0 µm vesicles were filtered through a 1.0 micron polycarbonate filter. The size of the vesicles decreased to 2.4±0.36 µm.

B. Characterization of Polymersomes

The structure of an exemplified polymersome vesicle can be characterized by the following generalized method. In a preferred embodiment, 1% (w/w) of the amphiphile is solubilized in aqueous solution, and the vesicles self-assemble during the solubilization process. Thin films (ca. 100 run) of the vesicular solution suspended within the pores of a microperforated grid are prepared in an isolated chamber with controlled temperature and humidity (Lin et al., *Langmuir*, 8:2200 1992). The sample assembly is then rapidly vitrified with liquid ethane at its melting temperature (~90 K), and then kept under liquid nitrogen until loaded onto a cryogenic sample holder (Gatan 626) (Lin et al., (1992)).

The morphologies of the polymersomes may be visualized by cryo-transmission electron microscopy (cryo-TEM or CTEM), by transmission electron microscopy (TEM), such as on a Phillips EM4 10 transmission electron microscope operating at an acceleration voltage of 80–100 kV, by inverted stage microscopy, or by any other means known in the art for visualizing vesicles. Cryo-TEM images revealed, at 1 nm resolution, the mean lamellar thickness of the hydrophobic core, which was ~8 to 9 nm for both the $EO_{40}$-$EE_{37}$ and $EO_{26}$-$PD_{46}$ membranes as listed in TABLE 2.

Small angle X-ray and neutron scattering (SAXS and SANS) analyses are well suited for quantifying the thickness of the membrane core (Won et al., 1999) or any internal structure. SAXS and SANS can provide precise characterization of the membrane dimensions, including the conformational characteristics of the PEO corona that stabilizes the polymersome in an aqueous solution. Neutron contrast is created by dispersing the vesicles in mixtures of $H_2O$ and $D_2O$, thereby exposing the concentration of water as a function of distance from the hydrophobic core.

Size distribution can be determined directly by microscopic observation (light and/or electron microscopy), by dynamic light scattering, or by other known methods. Polymersome vesicles can range in size from tens of nanometers to hundreds of microns in diameter. According to accepted terminology developed for lipid vesicles, small vesicles can be as small as about 1 nm in diameter to over 100 nm in diameter, although they typically have diameters in the tens of nanometers. Large vesicles range from 100 to 500 nm in diameter. Both small and large vesicles are best perceived as such by light scattering and electron microscopy. Giant vesicles are generally greater than 0.5 to 1 µm in diameter, and can generally be perceived as vesicles by optical microscopy.

Small vesicles can be as small as 1 nm in diameter to over 100 nm in diameter, although they typically have diameters in the tens of nanometers. Large vesicles range from 100 to 1000 nm in diameter, preferably from 500 to 1000 nm. Giant vesicles are generally greater than 1 µm in diameter. The preferred polymersome vesicles range of 20 nm to 100 µm, preferably from 1 µm to 75 µm, and more preferably from 1 µm to 50 µm.

The disclosed methods of preparation of the polymersomes are particularly preferred because the vesicles are prepared without the use of co-solvent. Any organic solvent used during the disclosed synthesis or film fabrication method has been completely removed before the actual vesicle formation. Therefore, the polymersomes of the present invention are free of organic solvents, distinguishing the vesicles from those of the prior art and making them uniquely suited for bio-applications.

The methods of analysis applied in a preferred embodiment of the invention provide a clear basis for applications of mass retention, delivery, and extraction, which may require membrane biocompatibility, and which may or may not take advantage of the novel thermal, mechanical, or chemical properties of the membranes. By "biocompatible" is meant a substance or composition which can be introduced into an animal, particularly into a human, without significant adverse effect. For example, when a material, substance or composition of matter is brought into a contact with a viable white blood cell, if the material, substance or composition of matter is toxic, reactive or biologically incompatible, the cells will perceive the material as foreign, harmful or immunogenic, causing activation of the immune response, and resulting in immediate, visible morphological changes in the cell. A "significant" adverse effect would be one which is considered sufficiently deleterious as to preclude introducing a substance into the patient.

Figure 8:
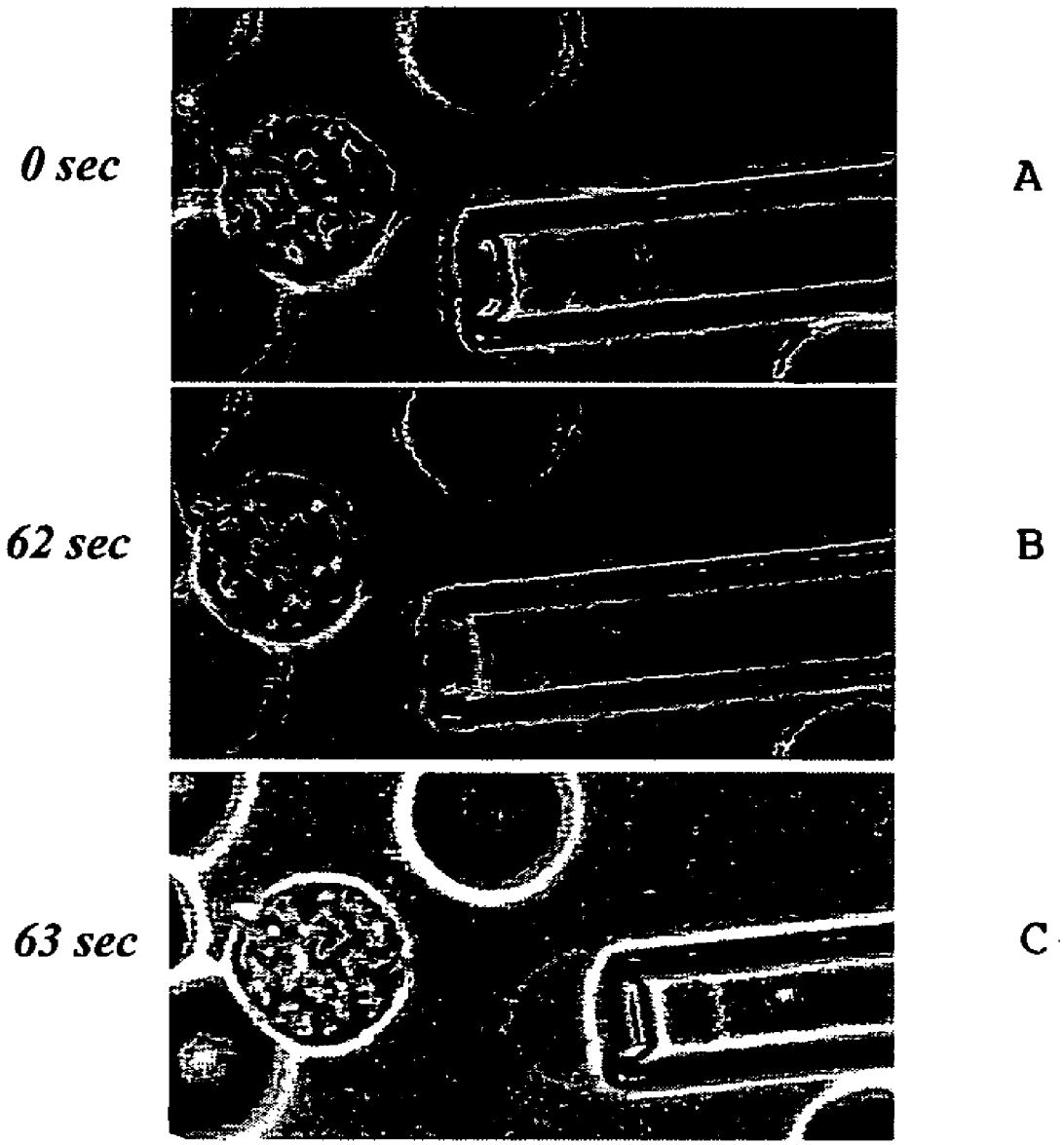
FIG. 8 depicts a biocompatibility test in which both red cells and polymersomes were suspended in 250 mOsm phosphate buffered saline in an opened chamber to determine cell adhesion. A polymersome was manipulated by a micropipette ($R_p$=2 μm) into contact with a granulocyte. Initial contact at time point 0 is shown in FIG. 8A.

To confirm one level of biocompatibility of the polymersomes, preliminary evaluations were performed by bringing the polymersomes into contact with white blood cells, such as granulocytes, as seen in FIG. 8A. Even after prolonged contact (over one minute) with the polymersomes, the white cells remained intact and unchanged (FIGS. 8B and 8C). No adhesion was observed, and the polymersomes caused no activation of the white blood cells, thus demonstrating the biocompatibility of the polymersomes.

If there were adhesion between vesicles and blood cells, micropipette aspiration could also be used to measure the inter-lamellar adhesion energy. If two vesicles or a cell and vesicle are manipulated into contact and adherent, then the inter-lamellar adhesion energy density y is determined from Young's equation, $\gamma=\tau(1-\cos\theta)$, where $\theta$ is the measurable contact angle between the two surfaces, $\tau$ is the tension required to peel the membranes apart. In the case of adhesion being strong enough to induce membrane cohesion, aspiration can again be used to directly observe the resulting coalescence of two vesicles (fusion), as well as the adsorption and intercalation of soluble objects (such as, surfactants or micelles) into the membrane.

C. Encapsulation into Polymersomes

An enormously wide range of materials can be encapsulated within a polymersome vesicle. In fact, to date no molecule has been found that cannot be encapsulated. Among the exemplary molecules that have been encapsulated are: proteins and proteinaceous compositions, e.g., myoglobin, hemoglobin and albumin, sugars and other representative carriers for drugs, therapeutics and other biomaterials, e.g., 10 kDa dextran, sucrose, and phosphate buffered saline, as well as marker preparations. Encapsulation applications range, without limitation from, e.g., drug delivery (aqueously soluble drugs), to optical detectors (fluorescent dyes), to the storage of oxygen (hemoglobin).

A variety of fluorescent dyes of the type that can be incorporated within the polymersomes could include small molecular weight fluorophores, such as FITC, and fluorophores attached to dextrans of a laddered sequence of molecular weights. Imaging of the fluorescent core can be accomplished by standard fluorescent videomicroscopy. Permeability of the polymersome to the fluorophore can be measured by manipulating the fluorescently-filled vesicle with aspiration, and monitoring the retention of fluorescence against a measure of time.

Phosphate buffered saline (PBS; 10 mM phosphate buffer, 2.7 mM KCl, and 137 M NaCl) and other electrolytes, such as, but not limited to, KF or KI can be added during the vesicle preparation and be easily encapsulated by rehydration. The electroformation method is not very efficient in the presence of electrolytes.

Figure 7:
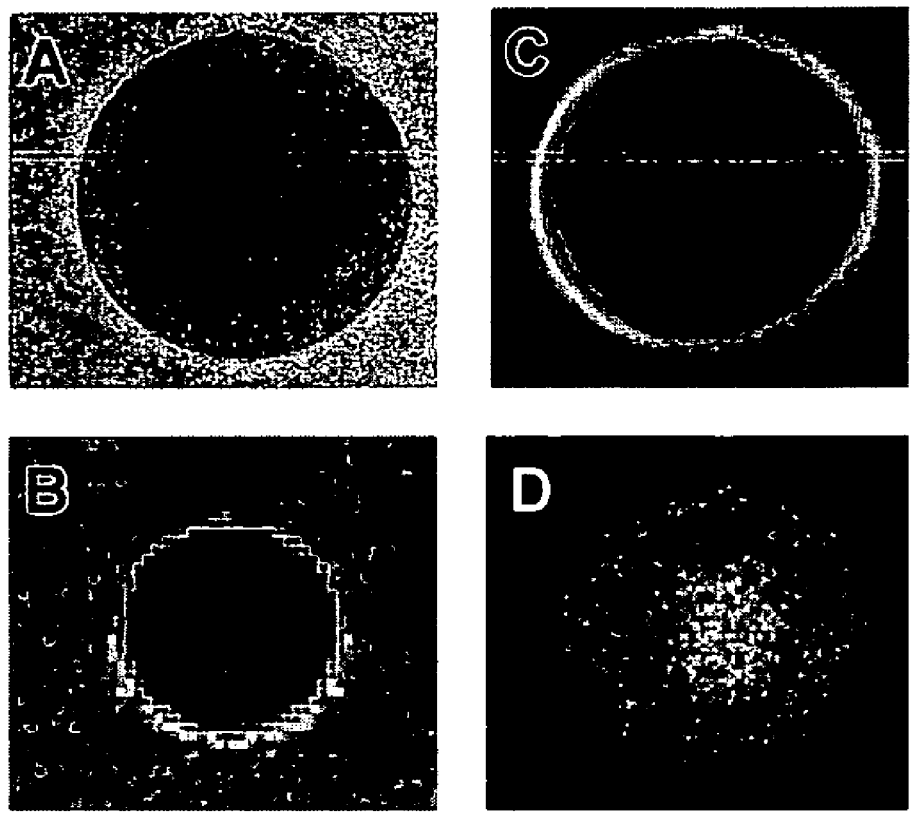
FIG. 7 demonstrates the encapsulation of globular proteins.

FIG. 7 demonstrates the encapsulation of globular proteins by film rehydration. As shown, $EO_{40}$-$EE_{37}$ vesicles were electroformed with 10 g/L myoglobin dissolved in 289 mOsm sucrose solution (FIG. 7A), and with 10 g/L hemoglobin dissolved in 280 mOsm PBS/sucrose solution (FIG. 7B). FIGS. 7C and 7D show a polymer vesicle containing fluorescein-tagged bovine serum albumin (BSA) encapsulated at 0.5 g/l.

D. Cross-linking of the Polymersomes

In a preferred embodiment, the invention provides reactive amphiphiles that can be covalently cross-linked together, over a many micron-squared surface, while maintaining the semi-permeability of the membrane. Cross-linked polymersomes are particularly useful in applications requiring stability of the vesicle membranes and durable retention of the encapsulated materials. By cross-linked is meant covalently interconnected; i.e., completely cross-linked vesicle have all the membrane components covalently interconnected into a giant single molecule; cross-linked vesicles have interconnected components throughout their entire surface; and partly cross-linked vesicles contain patches of the interconnected components.

Cross-linking of the amphiphiles can be achieved using double bond-containing blocks, such as polybutadiene, which can be readily coupled by standard cross-linking reactions. In a preferred embodiment of the present invention, the vesicles are cross-linked by free radicals generated with combination of an initiator, such as $K_2S_2O_8$, and a redox coupler, such as $Na_2S_2O_5/FeSO_4.7H_2O$ (Won et al., 1999). Although any suitable pairing of an initiator and a redox coupler may be selected by one of ordinary skill in the art to cause the cross-linking reaction, the suggested compounds have been found to be particularly suited to effect the cross-linking of the exemplified amphiphiles of the present invention. In the preferred and exemplified embodiment, the osmolarity of the cross-linking reagents is adjusted to match the osmolarity of the encapsulated material, and the components are mixed in the following order and volume ratios relative to sample: $K_2S_2O_8:Na_2S_2O_5:FeSO_4=1:0.5:0.02$. Due to instabilities of the sulfates, $K_2S_2O_8$ and $Na_2S_2O_5$ must be prepared within a few days of performing the reaction and $FeSO_4$ within several minutes of its use to ensure efficient cross-linking of the amphiphiles.

Of course, the cross-linking mechanism need not to be limited to redox reaction methods, such as the one disclosed above. Cross-linking can be carried out by a variety of alternative and known techniques, including but not limited to, $^{60}Co$ $\gamma$-irradiation (Hentze et al., *Macromolecules* 32: 5803–5809 (1999)), or by visible or UV light irradiation with an incorporated sensitizer, such as 3,3,3',3'-tetramethyldiocta-decyl indocarbocyanine ($DiI(C_{18})$). ($DiI(C_{18})$ is an amphiphilic sensitizing dye which can generate oxygen free radicals when irradiated with green or UV light (Mueller et al., *Polymer Preprints (ACS)* 40(2):205 (1999)). It has already been established that this particular dye, as well as other dyes, can be incorporated into the polymersome membrane during vesicle preparation, or even after vesicle formation, in relatively large amounts as observed by fluorescent microscopy.

E. Permeability of the Polymersome Membrane, and Transport of Encapsulated Material (1) Water Permeability Polymersomes, as exemplified by $EO_{40}$-$EE_{37}$, can be substantially less permeable to water than phospholipid membranes, which suggests many beneficial applications for the polymersomes. To measure the permeability of a polymersome to water, observations were made of the time course for vesicle swelling in response to a step change in external medium osmolarity. Briefly, vesicles were prepared in the preferred and exemplified embodiment in 100 mOsm sucrose solution to establish an initial, internal osmolarity, after which they were suspended in an open-edge chamber formed between cover slips, and containing 100 mOsm glucose. A single vesicle was aspirated into a micropipette with a suction pressure sufficient to smooth membrane fluctuations. The pressure was then lowered to a small holding pressure. Using a second, transfer pipette, the vesicle was moved to a second chamber containing 120 mOsm glucose.

When water flows out of the vesicle due to the osmotic gradient between inside and outside of the vesicle, the result is an increased projection length $L_P$, which is monitored over time. The exponential decrease in vesicle volume can be calculated from video images, and then fit to determine the permeability coefficient ($P_f$) (see, e.g., Bloom et al., 1991; Needham et al., 1996). The permeability coefficient, $P_f$, determined for $EO_{40}$-$EE_{37}$ was 2.5±1.2 µm/s, which, when compared with representative vesicles of stearyloleoyl-phosphatidylcholine (SOPC) that have $P_f$=23.5±1.7 µm/s from comparable methods, indicates a significant reduction in the permeability of the polymersomes.

The reduced permeability results mainly from the increased hydrophobic thickness. On a per area basis, $EO_{40}$-$EE_{37}$ membranes and phospholipid membranes were found to exhibit similar fluctuations in area as understood from the fact that the membranes have a comparable area expansion modulus. Consequently, the ratio of permeabilities largely reflects the relative probability for water to diffuse across the membrane, and the ratio of diffusion times should decrease with relative thickness of the hydrophobic core as $\exp(-d_{OE7}/d_{lipid})$. For polymersomes of $EO_{40}$-$EE_{37}$, this yields $\exp(-8 \text{ nm}/3 \text{ nm})=0.07$, which is a value close to the measured ratio of permeabilities for these polymersomes versus phospholipid vesicles.

The cross-linked membrane is also permeable to water. Observed volume changes due to an osmolarity difference between the inside and outside of cross-linked polymersomes are very similar to the volume changes of uncross-linked vesicles under the same conditions, suggesting that the permeability of the cross-linked membrane is quite similar to the measured value for the exemplified $EO_{40}$-$EE_{37}$ membranes. In addition, cross-linked vesicles can be completely dehydrated in air, without loss of solutes, and rehydration leads to swelling by water permeation through the membrane.

(2) Permeability of the Polymersome to Encapsulated Materials

Figure 5:
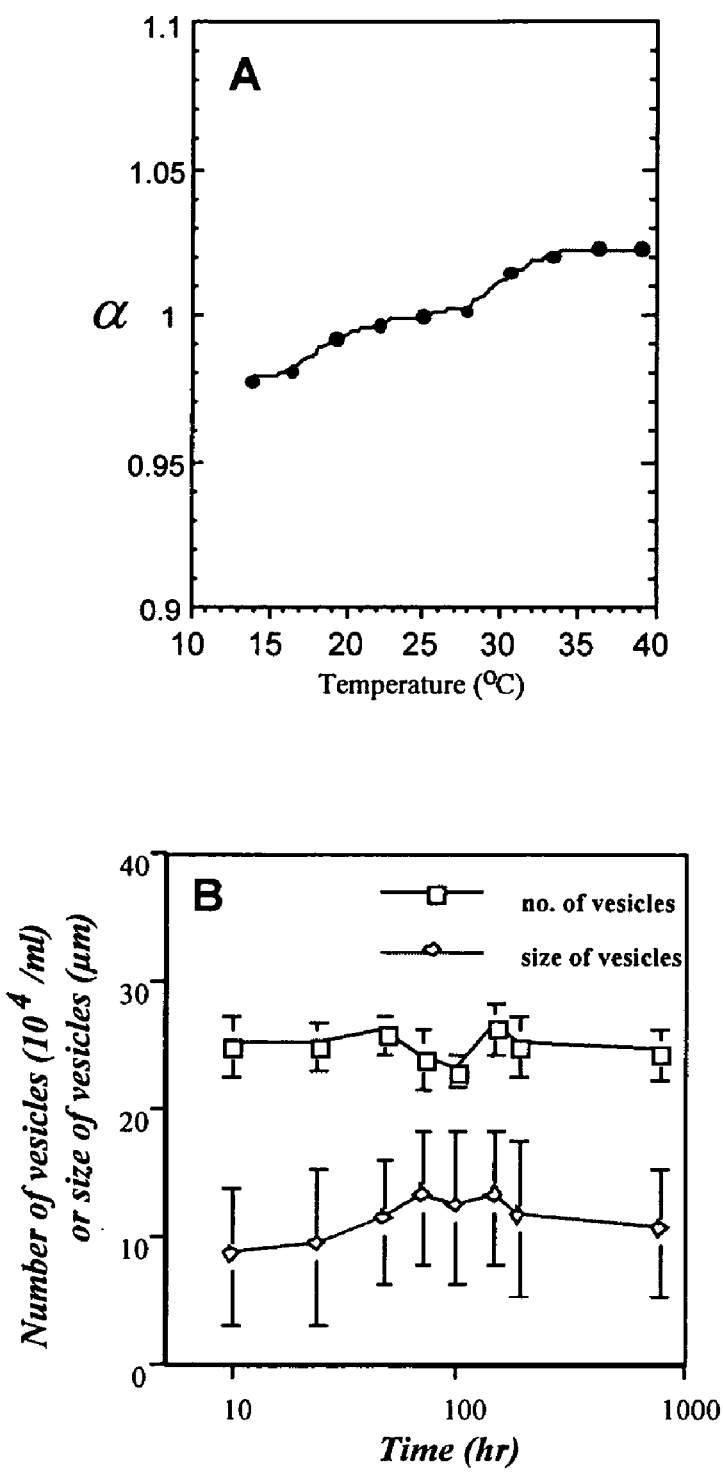
FIG. 5 indicates thermal and physiological solution stability of $EO_{40}$-$EE_{37}$ vesicles.
Figure 10:
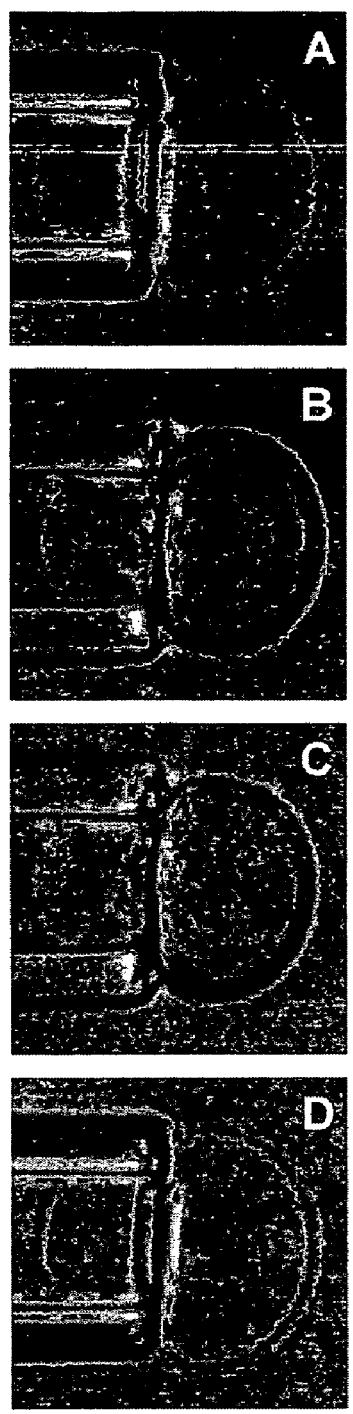
FIG. 10 depicts the stability of an $EO_{26}$-$BD_{46}$ vesicle in chloroform.

To verify the wide range of molecules encapsulated in the polymersomes, as described above, a method was devised using phase contrast microscopy to give rise to different intensities for materials with distinct optical indices, such as sucrose and phosphate buffered saline. No noticeable change was detected in the intensities or the differences between intensities over time periods from minutes to a month (FIG. 5B). The same was true for the intensities of fluorescently-labeled materials in fluorescent microscopy experiments. Therefore, the polymersome membrane is essentially impermeable to the encapsulated molecules. The impermeability of the cross-linked membrane was also confirmed by the finding that these vesicles retain their encapsulated sucrose, observable through phase contrast, even after complete dehydration and rehydration of the vesicle (FIG. 11), or after 30 minute exposure to chloroform (FIG. 10).

F. Stability of Polymersomes (1) Stability in Physiological Buffers

FIG. 5B demonstrates the long-term stability of $EO_{40}$-$EE_{37}$ polymersomes in phosphate buffered saline. Polymer vesicles were suspended in PBS, and their concentration estimated by counting the intact vesicles using a hemocytometer at different time points. At the same time, the size of the vesicles was determined as an average of twenty randomly selected vesicles. No significant change in the concentration or size distribution of the polymersomes was observed over period of more than one month. Moreover, addition of ethanol to PBS had no significant effect on the polymersome concentration or size distribution, suggesting that such treatments can be use as sterilizing agents (TABLE 3).

(2) Thermal Stability

As shown in TABLE 4, however, the thermal stability of $EO_{40}$-$EE_{37}$ vesicles was severely tested when the vesicles were exposed to autoclave temperatures and pressures (121° C., at 2 atm) for 15 minutes. Some vesicles maintained a phase contrast and could be counted as largely retaining their contents. At the dilute polymersome concentrations used in these studies, the results clearly show that a significant fraction (about 10%) of polymersomes can survive a sterilizing treatment such as autoclaving.

TABLE 4

Tabulation of phase dense vesicles after autoclaving

| Trial # | Before Autoclave | | After Autoclave | |
|---|---|---|---|---|
| | No. of vesicles $10^4$/ml | size distribution (µm) | No. of vesicles $10^4$/ml | Size distribution (µm) |
| 1 | 82.4 | 7.3 ± 4.8 | 8.1 | 3.7 ± 0.4 |
| 2 | 94.3 | 6.0 ± 2.8 | 11.9 | 4.0 ± 0.6 |
| 3 | 120.6 | 8.2 ± 5.2 | 10.7 | 3.8 ± 0.5 |

FIG. 5A shows the thermal stability of $EO_{40}$-$EE_{37}$ vesicles, indicating the membrane's area expansion with increasing temperature, and its stability at 37° C., when the vesicle is held at a fixed membrane tension of less than 4 mN/m. The relative polymer vesicle area, α, is shown against temperature. The overall thermal expansivity is approximately $1.9 \times 10^{-3}$ per degree C.

To confirm the thermal stability of the cross-linked polymersomes, the exemplified cross-linked $EO_{26}$-$PD_{46}$ vesicles containing an encapsulated 250 mOsm sucrose solution were suspended in 250 mOsm glucose solution. About 0.5 ml of the vesicular solution was added to an Eppendorf test tube and submerged into boiling water for 15 minutes. The number of vesicles before and after boiling was quantified with hemocytometer, and the numbers were found to remain constant at the original level of $10^5$/ml. Thus, the cross-linked $EO_{26}$-$PD_{46}$ vesicles are thermally stable at 100° C. for at least 15 minutes. Moreover, the increase in temperature to 100° C. did not alter the phase contrast image of the encapsulated sucrose, confirming that the impermeability of the polymersome membrane is retained at temperatures as high as 100° C.

(3) Stability in Organic Solvents

To confirm the stability of the polymersomes in organic solvents, the exemplified cross-linked $EO_{26}$-$PD_{46}$ vesicles were inserted into one of the copolymer's best solvents, chloroform, and observed. Insertion of vesicles into a droplet of chloroform carefully placed in the micromanipulation chamber altered neither the vesicle's size, nor its shape, and the vesicle membrane remained stable for as long as it was kept in the solvent (up to 30 minutes) (FIG. 10). Small, scattering objects appeared inside the cross-linked vesicles when they were placed in contact with chloroform (FIGS. 10B and 10C). However, the particles disappeared when the vesicle was returned to aqueous solution (FIG. 10D). The scattering objects simply indicate, most likely, a finite permeability of the membrane to chloroform and formation of an encapsulated chloroform-in-water microemulsion. Moreover, examination of the vesicles under phase contrast microscopy directly confirmed that they retain large solute molecules, such as sucrose, which also has a significant solubility in chloroform (approximately millimolar).

By contrast, uncross-linked vesicles ruptured, even before they could be transferred by micropipette into the chloroform droplet. This is because the small solubility of chloroform in water (about 0.5% by volume) leads to a concentration gradient near the interface, and even this small chloroform concentration several microns away from the interface, is sufficient to selectively disrupt an uncross-linked vesicle.

(4) Stability to Dehydration and Rehydration

An additional stability test was conducted to confirm the remarkable stability of the cross-linked polymersomes to dehydration. Due to the non-zero permeability of the cross-linked $EO_{26}$-$PD_{46}$ vesicles to water, these vesicles can be completely dehydrated in a test tube. The dry vesicles can be stored in air at room temperature for more than 24 hours and then rehydrated by addition of water to restore the vesicle to its original volume. No noticeable difference between the original and rehydrated vesicles was been found.

Figure 11:
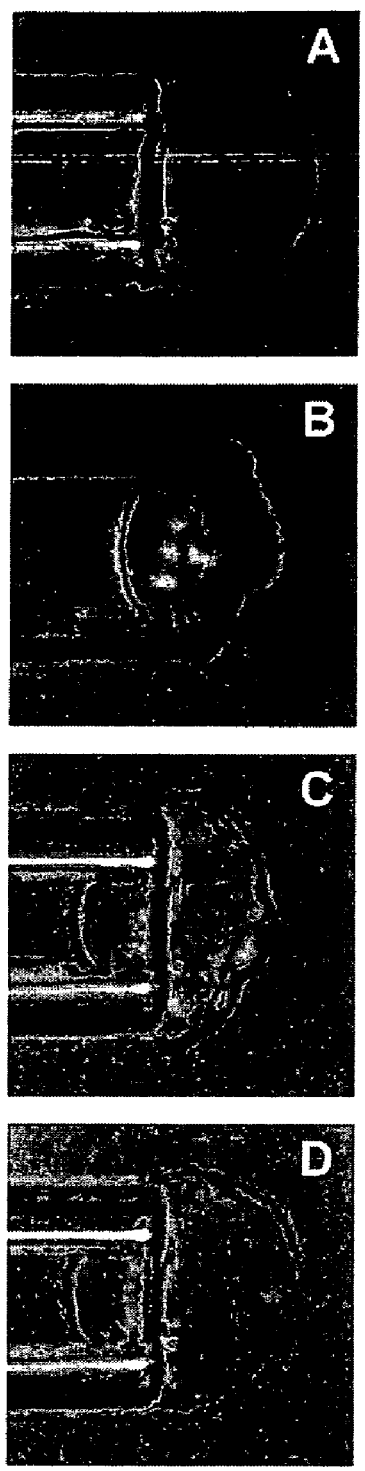
FIG. 11A depicts a vesicle in aqueous solution pulled into a micropipette ($R_p$=3.5 μm) by negative pressure, $\Delta P$.
FIG. 11B depicts the same vesicle imaged within seconds after its removal from the aqueous solution and exposure to the air. By comparison, as depicted in FIG. 11C, rehydration occurs immediately upon reinsertion of the same vesicle back into the aqueous solution. The original shape is nearly restored within 1 minute, as depicted in FIG. 11D, indicating the retention of solutes.

Individual vesicles can be also aspirated into a micropipette and pulled from aqueous solution into the open air (FIG. 11). As the water evaporates, the volume of the vesicle decreases, and the membrane collapses. The semi-dehydrated vesicle can be inserted back into aqueous solution and rehydrated to its original shape. Phase contrast microscopy confirmed that the encapsulated material, such as sucrose, remains inside the dry vesicles. Therefore, the vesicles can be used in applications that require long-term storage of material.

It is clear from the foregoing, that polymersomes are particularly useful for the transport (either delivery to the bulk or removal from the bulk) of hormones, proteins, peptides or polypeptides, sugars or other nutrients, drugs, medicaments or therapeutics, including genetic therapeutics, steroids, vitamins, minerals, salts or electrolytes, genes, gene fragments or products of genetic engineering, dyes, adjuvants, biosealants and the like. In fact, the stable vesicle morphology of the polymersome may prove particularly suited to the delivery of biosealants to a wound site. In bioremediation, the polymersomes could effectively transport waste products, heavy metals and the like. In electronics, optics or photography, the polymersomes could transport chemicals or dyes. Moreover, these stable polymersomes may find unlimited mechanical applications including insulation, electronics and engineering.

In addition, the polymersome vesicles are ideal for intravital drug delivery because they are biocompatible; that is they contain no organic solvent residue and are made of nontoxic materials that are compatible with biological cells and tissues. Thus, because they can interact with plant or animal tissues without deleterious immunological effects, any drug deliverable to a patient could be incorporated into a biocompatible polymersome for delivery. Adjustments of molecular weight, composition and polymerization of the polymer can be readily adapted to the size and viscosity of the selected drug by one of ordinary skill in the art using standard techniques.

Additional encapsulation applications that involve incorporation of hydrophobic molecules in the bilayer core include, e.g., alkyd paints and biocides (e.g., fungicides or pesticides), obviating the need for organic solvents that may be toxic or flammable. Polymersomes also provide a controlled microenvironment for catalysis or for the segregation of non-compatible materials.

The vesicles of the present invention further provide useful tools for the study of the physics of lamellar phases. At different temperatures or reduced volumes (achieved by deflating the vesicle interior with an external high salt solution), such vesicles will display a variety of shapes. The formation of these shapes is dictated by the minimization of energy of deformation of the vesicle, namely the curvature and area elasticity of the membrane. In fact, a series of theoretical models, called "area-difference elasticity" (ADE) models, have been used to predict a limited spectrum of different shapes seen with vesicles, such as buds, pear-shaped vesicles and chains. Comparison between observed shapes and theoretical calculations are used to verify theoretical concepts of how lamellar phases behave, e.g., features such as the curvature, or the tendency of molecules to "flip-flop" between monolayers.

In addition, polymersomes have a small negative buoyancy making them subject to gravitational shape deformations. Therefore, polymersomes afford interesting models for studying the effects of gravitation, or the lack thereof.

The present invention is further described in the following examples. These examples are not to be construed as limiting the scope of the appended claims.

EXAMPLES

Example 1

Polymersomes from Amphiphilic Diblock Copolymers

Membranes assembled from a high molecular weight, synthetic analog (a super-amphiphile) are exemplified by a linear diblock copolymer $EO_{40}$-$EE_{37}$. This neutral, synthetic polymer has a mean number-average molecular weight of about 3900 g/mol mean, and a contour length ~23 nm, which is about 10 times that of a typical phospholipid acyl chain (FIG. 1A). The polydispersity measure, $M_w/M_n$, was 1.10, where $M_w$ and $M_n$ are the weight-average and number-average molecular weights, respectively. The PEO volume fraction was $f_{EO}$=0.39, per TABLE 1.

Adapting the electroformation methods of Angelova et al., 1992, a thin film (about 10 nm to 300 nm) was prepared. Giant vesicles attached to the film-coated electrode were visible after 15 to 60 min. These were dissociated from the electrodes by lowering the frequency to 3 to 5 Hz for at least 15 min and by removing the solution from the chamber into a syringe. The polymersomes were stable for at least month if kept in vial at room temperature. The vesicles also remained stable when resuspended in physiological saline at temperatures ranging from 10E to 50EC.

Images were obtained with a JEOL 1210 at 120 kV using a nominal underfocus of 6 μm and digital recording. Imaging of the hydrophobic cores of these structures revealed a core thickness d=8 nm, which is significantly greater than d=3 nm for phospholipid bilayers as described in the *Handbook of Biological Physics*, 1995.

Thermal undulations of the quasi-spherical polymersome membranes provided an immediate indication of membrane softness (FIG. 2A). Furthermore, when the vesicles were made in the presence of either a 10-kD fluorescent dextran (FIG. 2B), sucrose or a protein, such as globin, the probe was found to be readily encapsulated and retained by the vesicle for at least several days. The polymersomes further proved highly deformable, and sufficiently resilient that they could be aspirated into micrometer-diameter pipettes (FIGS. 2C and 2D). The micromanipulations were done with micropipette systems as described above and analogous to those described by Longo et al., 1997 and by Discher et al., *Science* 266:1032 (1994).

The elastic behavior of a polymersome membrane in micropipette aspiration (at ~23° C.) appeared comparable in quality to a fluid-phase lipid membrane. Analogous to a lipid bilayer, at low but increasing aspiration pressures, the thermally undulating polymersome membrane was progressively smoothed, increasing the projected area logarithmically with tension, $\tau$, (FIG. 3A). From the slope of this increase (in tension units of mN/m) versus the fractional change, $\alpha$, in vesicle area the bending modulus, $K_b$, was calculated (see, e.g., Evans et al., *Phys. Rev. Lett.* 64:2094 (1990); Helfrich et al., *Nuovo Cimento* D3:137 (1984)).

$$K_b \approx k_B T \ln(\tau)/(8\pi\alpha) + \text{constant} \quad (1)$$

Figure 3:
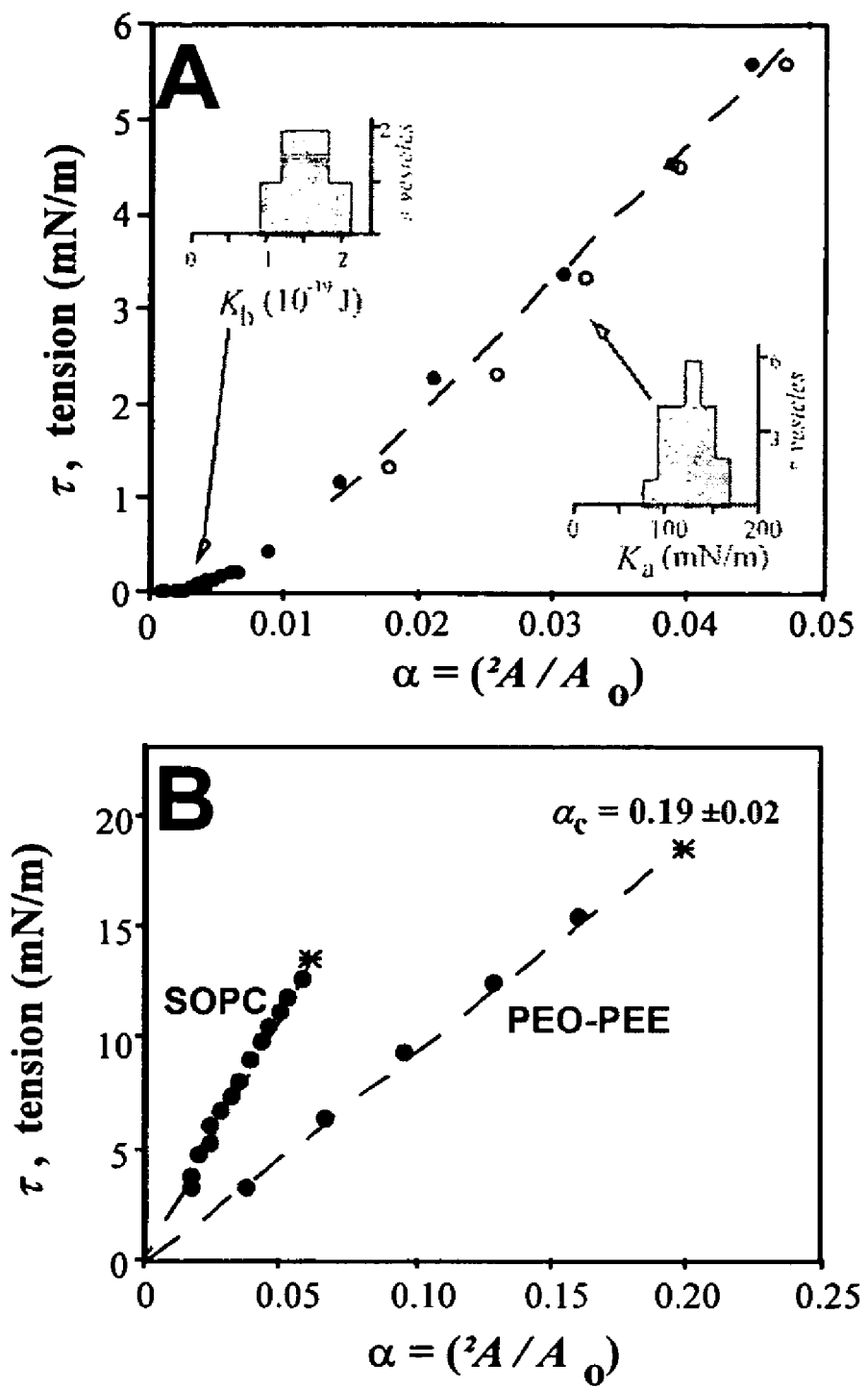
FIG. 3 graphically depicts the mechanical properties of polymersome membranes as assessed by micromanipulation.

When calculated, it was found to be $1.4 \pm 0.3 \times 10^{-19}$ Joules (J), based upon the measurements of six vesicles. In equation 1, $k_B$ is Boltzmann's constant and T is an absolute temperature. Above a crossover tension, $\tau_x$, an area expansion modulus, $K_a$, was estimated with $$K_a = \tau/\alpha \quad (2)$$

applied to the slope of the aspiration curve as illustrated in FIG. 3.

Aspiration in this regime primarily corresponds to a true, as opposed to a projected, reduction in molecular surface density, and for the polymersome membranes, $K_a = 120 \pm 20$ mN/m (based upon 21 vesicles). Fitted moduli were checked for each vesicle by verifying that the crossover tension, $\tau_x = (K_a/K_b)(k_B T/8\pi)$, (Evans et al., 1990) suitably fell between appropriate high-tension (membrane stretching) and low-tension (membrane smoothing) regimes.

Measurements of both moduli, $K_a$ and $K_b$, were further found to yield essentially unimodal distributions with small enough standard deviations (approximately 20% of mean) to be considered characteristic of unilamellar polymer PEO—PEE vesicles. Interestingly, the moduli are also well within the range reported for various pure and mixed lipid membranes. SOPC (1-stearoyl-2-oleoyl phosphatidylcholine) in parallel manipulations was found, for example, to be approximately $K_a = 180$ mN/m (FIG. 3B) and $K_b = 0.8 \times 10^{-19}$ J. Lastly, at aspiration rates where projection lengthening was limited to <1 μm/s, the microdeformation proved largely reversible, consistent again with an elastic response.

The measured $K_a$ is most simply approximated by four times the surface tension, $\gamma$, of a pure hydrocarbon-water interface ($\gamma = 20$ to 50 mJ/m$^2$), and thus reflects the summed cost of two monolayers in a bilayer (see, e.g., Israelachvili, in *Intermolecular and Surface Forces*, 2$^{nd}$ ed., Sec. III, 1995). The softness of $K_a$ compared with gel or crystalline states of lipid systems is further consistent with liquid-like chain disorder as described by Evans et al., 1987. Indeed, because the average interfacial area per chain, $<A_c>$, in the lamellar state has been estimated to be $<A_c>/2.5$ nm$^2$ per molecule (see, e.g., Hajduk et al., 1998; Warriner et al., *Science* 271: 969 (1996); Yu et al., 1998), the root-mean-squared area fluctuations at any particular height within the bilayer can also be estimated to be, on average, $<\delta A_c^2>^{1/2} = (<A_c>k_B T/K_a)^2/0.3$ nm$^2$ per molecule, which is a significant fraction of $<A_c>$ and certainly not small on a monomer scale.

Moreover, presuming in the extreme, a bilayer of unconnected monolayers d/2 thick, with d estimated from cryo-TEM (FIG. 1), the PEE contour length is more than twice the monolayer core thickness, and therefore, configurationally mobile along its length. In addition, molecular theories of chain packing in bilayers have suggested that, although at a fixed area per molecule there is a tendency for $K_b$ to increase with chain length (that is, membrane thickness), other factors such as large $<A_c>$ can act to reduce $K_b$ (see, e.g., Szleifer et al., *Phys. Rev. Lett.* 60:1966 (1988); Ben-Shaul, in *Structure and Dynamics of Membranes from Cells to Vesicles*, in *Handbook of Biological Physics*, vol. 1, chap. 7 (Elsevier Science, Amsterdam, 1995)). Thus, despite the large chain size of $EO_{40}$-$EE_{37}$, a value of $K_b$ similar to that of lipid bilayers is not surprising.

Related to the length scales above, the root ratio of moduli, $(K_b/K_a)^{1/2}$, is generally recognized as providing a proportionate measure of membrane thickness (see, e.g., *Handbook of Biological Physics*, supra; Bloom et al., 1991; Needham et al., 1996, chap. 9; and Petrov et al., *Prog. Surf. Sci.* 18:359 (1984)). For the presently described polymersome membranes, $(K_b/K_a)^{1/2} = 1.1$ nm on average. By comparison, fluid bilayer vesicles of phospholipids or phospholipids plus cholesterol, have reported a ratio of $(K_b/K_a)^2 = 0.53$ to 0.69 nm (Evans et al., 1990; Helfrich et al., 1984). Typically, the fluid bilayer vesicles of phospholipids plus cholesterol have a higher $K_a$ than those of phospholipid alone.

A parsimonious continuum model for relating such a length scale to structure is based on the idea that the unconnected monolayers of the bilayer have, effectively, two stress-neutral surfaces located near each hydrophilic-hydrophobic core interface (see e.g., Petrov et al., *Prog. Surf Sci.* 18:359 (1984)). If one assumes that a membrane tension resultant may be located both above and below each interface, then $$(K_b/K_a) = \delta_H \delta_C \quad (3)$$

where $\delta_H$ and $\delta_C$ are, respectively, distances from the neutral surfaces into the hydrophilic and hydrophobic cores.

For lipid bilayers with d/2=1.5 nm and hydrophilic head groups equal to 1 nm thick, estimates of $\delta_C = 0.75$ nm and $\delta_H = 0.5$ nm yield a root-product, $(\delta_H \delta_C)^{1/2} = 0.61$ This is consistent with experimental results. The numerical result for PEO—PEE membranes (1.1 nm) suggests that the stress resultants are centered further from the interface, but not necessarily in strict proportion to the increased thickness or the polymer length.

Elastic behavior terminates in membrane rupture at a critical tension, $\tau_c$, and areal strain, a $\alpha_c$. With lipids, invariably $\alpha_c = 0.05$. This is consistent, it appears, with a molecular theory of membranes under stress (see, e.g., Netz et al., *Phys. Rev. E* 53:3875 (1996) describing self-consistent calculation models of lipids). For the polymersomes, cohesive failure occurred at $\alpha_c = 0.19 \pm 0.02$ (FIG. 3B).

Another metric is the toughness or cohesive energy density that, for such a fluid membrane, is taken as the integral of the tension with respect to area strain, up to the point of failure:

$$E_c = \frac{1}{2} K_a \alpha_c^2 \quad (4)$$

For a range of natural phospholipids mixed with cholesterol, the toughness has been systematically measured, with $E_c$ ranging from 0.05 to 0.5 mJ/m$^2$ (see, Needham et al., 1990). By comparison, the $EO_{40}$-$EE_{37}$ membranes are 5 to 50 times as tough, with $E_c \approx 2.2$ mJ/m$^2$. On a per molecule, as opposed to a per area basis, such critical energies are remarkably close to the thermal energy, $k_B T$, whereas such an energy density for lipid bilayers is a small fraction of $k_B T$. This difference indicates, that for this relatively simple condensed matter system, the strong role that fluctuations in density have in creating a lytic defect.

Despite the comparative toughness of the polymersome membrane, a core "cavitation pressure," $p_c$, may be readily estimated as:

$$p_c = \tau_c/d \quad (5)$$

yielding a value of $p_c = -25$ atm. This value falls in the middle of the range noted for lipid bilayers, $p_c = -10$ atm to −50 atm (see, e.g., Bloom et al., 1991; Needham et al., 1996). Bulk liquids, such as water and light organics, are commonly reported to have measured tensile strengths of such a magnitude, as may be generically estimated from a ratio of nominal interfacial tensions to molecular dimensions (that is, ~γ/d). In membrane systems, this analogy again suggests an important role for density fluctuations, which are manifested in a small $K_a$, and which must become transversely correlated upon coalescing into a lytic defect.

Because the previous estimate for $<\delta A_c^2>^{1/2}$ is clearly not small as compared with the cross section of $H_2O$, a finite permeability of the polymersome membranes to water was expected. To verify this expectation polymersome permeability was obtained by monitoring the exponential decay in $EO_{40}$-$EE_{37}$ vesicle swelling as a response to a step change in external medium osmolarity. Vesicles were prepared in 100 mOsm sucrose solution to establish an initial, internal osmolarity, after which they were suspended in an open-edge chamber formed between cover slips and containing 100 mOsm glucose. A single vesicle was aspirated with a suction pressure sufficient to smooth membrane fluctuations; after which the pressure was lowered to a small holding pressure.

With a second, transfer pipette, the vesicle was moved to a second chamber with 120 mOsm glucose. Water flowed out of the vesicle due to the osmotic gradient between the inner and outer surfaces, which led to an increased projection length that was monitored over time. The exponential decrease in vesicle volume was calculated from video images, and then fit to determine the permeability coefficient ($P_f$) (see, e.g., Bloom et al., 1991; Needham et al., 1996). The permeability coefficient, $P_f$, was 2.5±1.2 μm/s.

In marked contrast, membranes composed purely of phospholipids with acyl chains of approximately 18 carbon atoms typically have permeabilities in the fluid state at least an order of magnitude greater (25 to 150 μm/s). Polymersomes are thus significantly less permeable to water, which suggests beneficial applications for the polymersomes.

Example 2

Crosslinked Polymersomes

Given the flexibility of copolymer chemistry, the stealth character as well as the cell stability can be mimicked with amphiphilic diblock copolymers that have a hydrophilic fraction comprising PEO, and a hydrophobic fraction which can be covalently cross-linked into a network. One example of a diblock copolymer having such properties, along with the capability of forming several morphologically different phases, is polyethylene oxide-polybutadiene (PEO—PBD).

$EO_{26}$-$BD_{46}$, spontaneously forms giant vesicles as well as smaller vesicles in aqueous solutions without the need of any co-solvent. Cross-linkable unilamellar vesicles were fabricated. The formed vesicles were cross-linked by free radicals generated with a of initiating $K_2S_2O_8$ and a redox couple $Na_2S_2O_5$/$FeSO_4$·$7H_2O$ as described above. When the osmolarity of the cross-linking reagents was kept the same as that of the vesicle solution, neither addition of the cross-linking reagents nor the cross-linking reaction itself affected vesicle shape.

Figure 9:
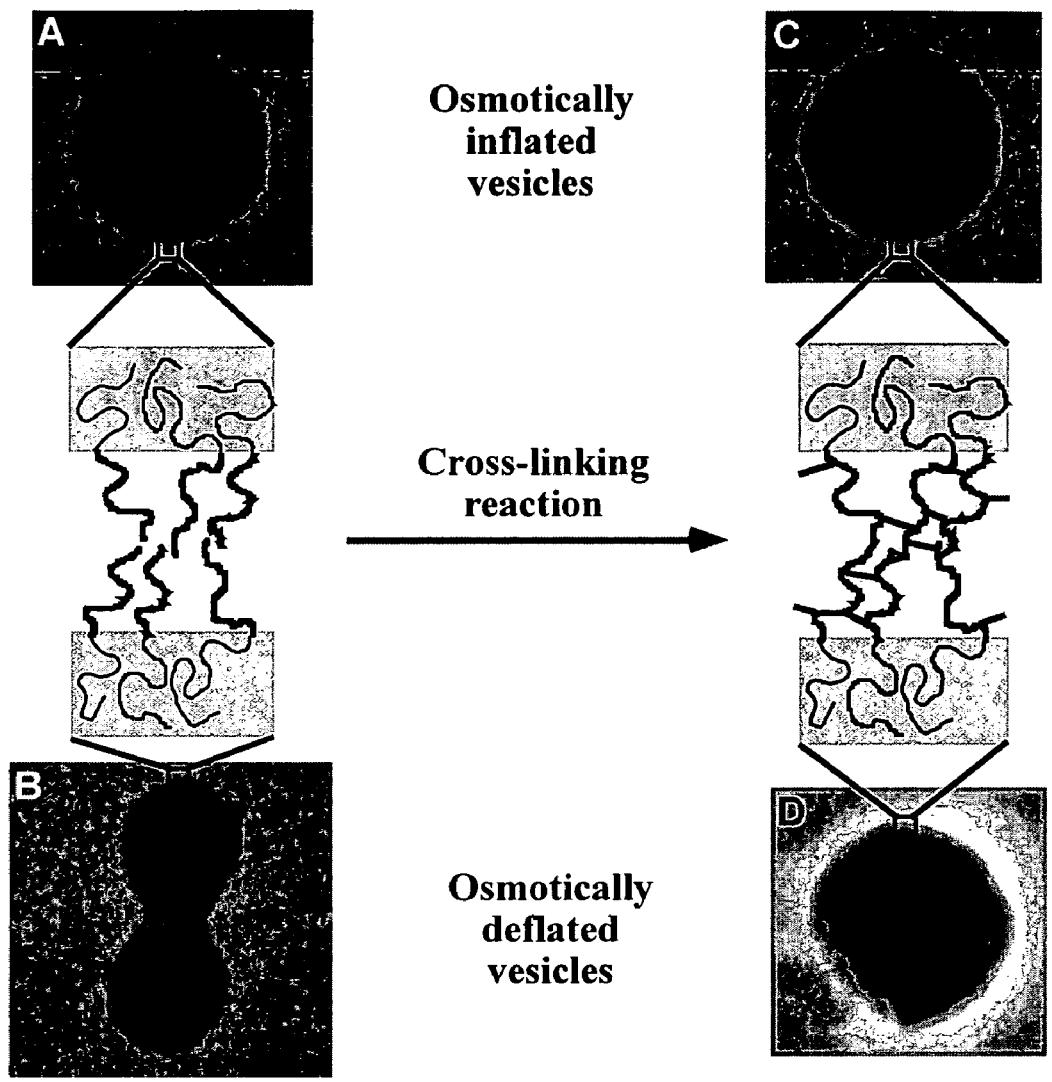
FIG. 9 depicts phase contrast images of unilamellar, 15 microns vesicles of $EO_{26}$-$BD_{46}$ with corresponding schematic representations of the membrane before the cross-linking reaction, wherein the osmotically inflated vesicles are spherical (FIG. 9A); and after the cross-linking reaction (FIG. 9C).

Osmotically inflated vesicles remained spherical, independent of the cross-linked state of the membrane (FIGS. 9A and 9C). Consequently, the fully inflated spheres, pearls of interconnected spheres, and other shapes appeared unchanged from the way they were observed prior to the cross-linking reaction. When fluid phase vesicles are osmotically deflated, the result is a flaccid shape, with a smooth contour (FIG. 9B). However, when the cross-linked vesicles were osmotically deflated after the cross-linking reaction was completed, the vesicles revealed the solid character of the membrane—with irregularly deformed creased structures (FIG. 9D). The difference reflected the fact that, when exposed to a change in osmolyte, the cross-linked molecules could not significantly rearrange within their surface to relax the accumulated strain.

The cross-linked $EO_{26}$-$BD_{46}$ vesicles were initially tested for stability by direct observation of the vesicles inserted into a solvent, chloroform. However, chloroform altered neither the size, nor the shape of the vesicles, and the vesicle membrane remained stable for as long as it was kept in the solvent. The mechanical properties of the vesicle when exposed to solvent are shown in FIG. 10. FIG. 10A depicts a vesicle in aqueous solution being pulled into a micropipette by negative pressure, ΔP. FIG. 10B depicts the same vesicle imaged immediately after being placed into chloroform. After 30 minutes exposure to chloroform, there was no noticeable change observed in the vesicle (FIG. 10C); and the vesicle remained unchanged after it was returned to the aqueous solution (FIG. 10D).

If a significant portion (few weight percent) of the solutes were lost from the vesicle during chloroform exposure, the aspirated projection of the vesicle would have lengthened. However, no detectable change occurred in either surface area or volume. This demonstrated that the cross-linked membrane maintains its integrity when exposed to organic solvent. By comparison, uncross-linked vesicles cannot be exposed without rupture to aqueous solutions containing a saturating concentration of solvent (approximately 0.8 g/dl chloroform).

A second stability test was based upon complete dehydration. Due to the finite water permeability of the cross-linked vesicles, they can be completely dehydrated in a test tube. Dry vesicles were stored in air, at room temperature, for more than 24 hours, then rehydrated by the addition of water to their original volume. However, no noticeable difference between the original and rehydrated vesicles was found.

Individual cross-linked vesicles were also aspirated into a micropipette, pulled from the aqueous solution (FIG. 11A) and exposed to the open air (FIG. 11B). As the water evaporated and the vesicle dehydrated, the volume decreased, and the membrane crinkled. Nevertheless, when the semi-dehydrated vesicle was returned to the aqueous solution, it was immediately rehydrated to its original shape (FIG. 11C). Within 1 minute of rehydration, the original shape of the dehydrated vesicle was almost completely restored, indicating the retention of solutes within the vesicle. Phase contrast microscopy further confirmed that encapsulated material, such as sucrose, remained inside the dry vesicles. Therefore, the cross-linked vesicles can be used in applications that require long-term storage of material.

Figure 12:
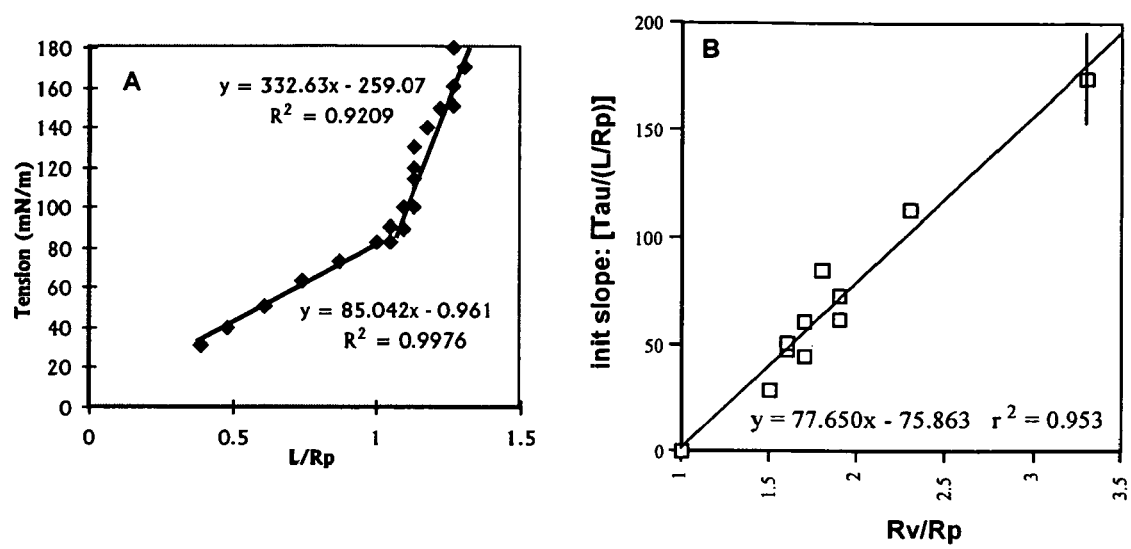
FIG. 12 illustrates the mechanical properties of the cross-linked polymersomes.

To finally confirm the stability of the cross-linked vesicles, deformation tests were done by micropipette manipulation (FIG. 12). The maximum applied aspiration pressure in the experimental setup, ΔP=1 atm, did not lead to rupture of the cross-linked vesicles. Since the typical micropipette radius in the experiment was 4 μm, such high pressures led to membrane tension at the cap, $\tau=\frac{1}{2}\Delta PR_p$ of around 200 mN/m, which is an order of magnitude higher than the lysis tension of red blood cells. A typical aspiration curve of a flaccid, nearly spherical (but not pressurized) vesicle is shown in FIG. 12A. Such aspiration curves can be done repeatedly, indicative of the membrane's elasticity.

Since the aspirated vesicles were flaccid, but almost spherical and non-pressurized, it was assumed that during initial aspiration, the area of the vesicle is constant, and that the bending becomes negligible with respect to shearing of the membrane. Given those assumptions, computer simulations for the shearing of the vesicle in the pipette indicated that the shear modulus is between one and two times the slope of $\tau/(L/R_p)$ versus $R_v/R_p$ (FIG. 12B). This was equal to about 150 mN/m, which is four orders of magnitude higher than the shear modulus of red blood cells, which was determined to be about 0.01 mN/m.

Although proving that a membrane is completely cross-linked is not a trivial task, and controversy is often associated with the subject, the stability tests reported in the present example provide the best direct evidence to date to confirm complete cross-linking. Cross-linking reactions introduce local stresses in the membrane, making it more difficult to completely cross-link a large (cell-size) structure that is self-assembled from monomers with a limited number of cross-linkable entities. However, by expanding the size of the polymerizable block in the present invention, the difficulties have been overcome.

Example 3

Polymersomes from Amphiphilic Triblock and Multi-Block Copolymers

Multi-block copolymers offer an alternative approach to modifying the properties of the polymersome. Insertion of a middle B block in a triblock copolymer permits modification of permeability and mechanical characteristics of the polymersome without chemical cross-linking. For example, if the B and C blocks are strongly hydrophobic, yet mutually incompatible, and the A block is water miscible, two segregated layers will form within the core of the membrane. This configuration of interfaces (internal B—C and external B-hydrated A) offers control of the spontaneous curvature of the membrane among other features such as height-localized cross-linking. Thus, vesicle size will depend, in part, on block copolymer composition. Of course, as noted above, the physical properties of the ABC polymersome will reflect a combination of the B, C and hydrated A mechanical behaviors. An example of such a triblock copolymer, which does form vesicles is $EO_{33}$-$S_{10}$-$I_{22}$ (TABLE 1), wherein EO is polyethyleneoxide, S is styrene, and I is isoprene.

Another arrangement for the triblock, which would form vesicles, is ABA or ABC wherein A and C are water miscible blocks and B is the hydrophobic block. In such case the copolymer can self-assemble in "straight" form into a monolayer or in "180° bent" form into a bilayer, or as a combination of these two forms. An example of this kind of ABA triblock, which does form vesicles, is $EO_{48}$-$EE_{75}$-$EO_{48}$ (TABLE 1).

Example 4

Vesicles of Mixed Composition

Vesicles comprising diblock copolymer mixtures have been prepared by the methods described above for a wide ratio of diverse amphiphilic components. As a first example, mixture of cross-linkable diblock copolymers with non-cross-linkable ones can be made. However, in contrast to the stabilizing effect of cross-linking on vesicles fabricated from purely cross-linkable amphiphiles as described above, the dilution of cross-linkable amphiphiles with non-cross-linkable molecules could produce a less stable membrane upon cross-linking, resulting in a controlled-release membrane.

For the purpose of this invention, the percolation threshold is a weight fraction of the cross-linkable copolymer above which the cross-linking reaction leads to a single cross-linked domain spanning the entire vesicle surface. Below the percolation threshold, a single cross-linked domain does not span the entire vesicle surface and is likely to be much less stable than a wholly cross-linked vesicle. For example, mixtures of $EO_{40}$-$EE_{37}$ and $EO_{26}$-$PD_{46}$ copolymers with the weight fraction of $EO_{26}$-$PD_{46}$ equal to 0.5 were found to be extremely fragile after the cross-linking reaction as compared with single component polymersome membranes (and therefore below the percolation threshold).

Figure 14:
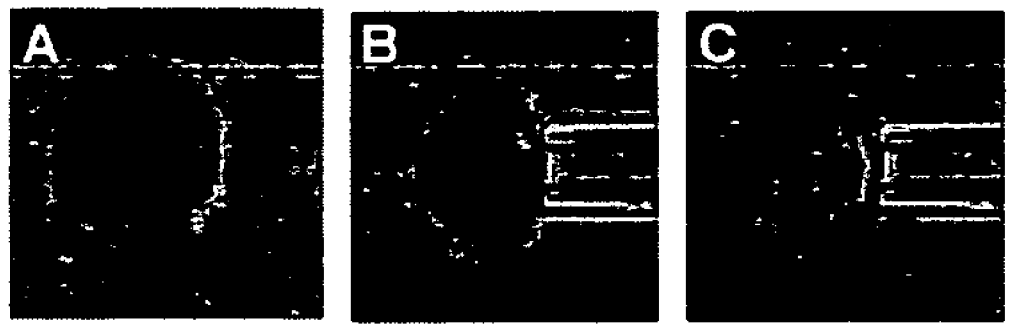
FIG. 14 depicts decreased stability of the vesicle fabricated from mixtures of $EO_{26}$-$BD_{46}$ and $EO_{40}$-$EE_{37}$.

Increase of the weight fraction to 0.6 caused the vesicles to be more stable than the uncross-linked membranes, but far more fragile than the vesicles composed of purely cross-linkable amphiphiles, as demonstrated by the leakage of encapsulated material (FIG. 14). Therefore, appropriate mixing of different components can be used to modulate vesicular stability. The destabilization by this type of cross-linking reaction can be applied to controlling the release of contents from the polymersome vesicle. Consequently, the polymersome can be induced to release an encapsulated component, either chemically and/or by wave propagation (such as, X-rays, UV, visible light, IR irradiation, and ultrasound).

Figure 6:
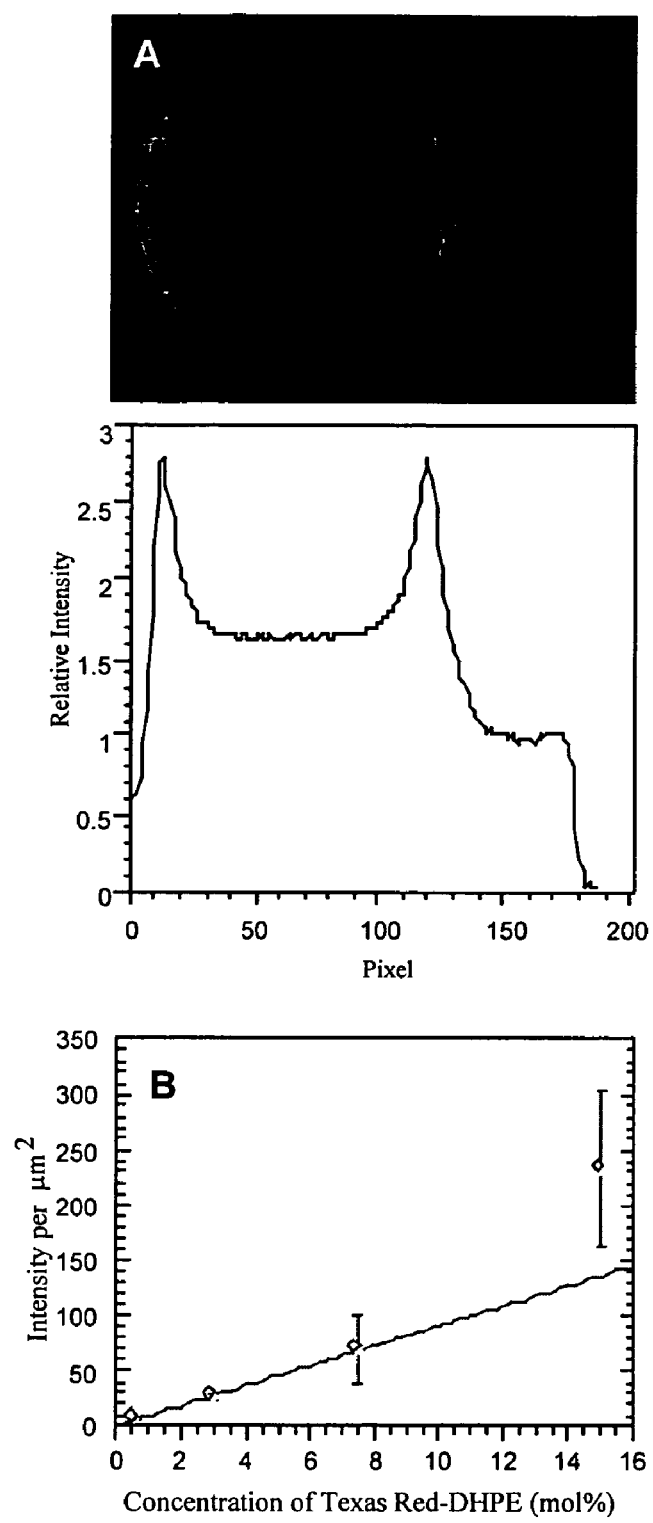
FIG. 6 shows a Texas Red-phosphatidylethanolamine (PE) lipid probe uniformly integrated into $EO_{40}$-$EE_{37}$ vesicles.

In the same way, mixtures can be made of the copolymer amphiphiles with other synthetic or non-synthetic amphiphiles, such as, lipids or proteins. For example, 3% of a Texas-Red labeled phosphatidylethanolamine preparation was incorporated into an $EO40$-$EE_{37}$ membrane with no obvious effect on either membrane structure or area expansion modulus (FIG. 6). FIGS. 6A and 6B show the uniformity of fluorescence around an aspirated contour of membrane with 3 mol % mixed in with polymer before vesicle formation. The uniformity of the fluorescence can be seen around an aspirated contour of the membrane demonstrating good mixing in the membrane.

Moreover, in FIG. 6C the contour intensity was seen to increase linearly as the concentration of Texas Red was increased to about 10 mol %, demonstrating ideal mixing of the components at that concentration range. Laser-photobleaching demonstrates that lipid probe diffusivity is 20-fold lower on average in the polymer membrane than in a lipid (SOPC) membrane which, by the present method has a diffusivity of approximately $3 \times 10^{-8}$ cm$^2$/s.

Based on the above features of amphiphile incorporation into polymersome membranes, the fluorescent lipophilic probe diI(C18) has been incorporated at a few mole percent into cross-linkable membranes and shown to yield unstable membranes after approximately 60 minutes of fluorescence excitation and photobleaching.

Example 5

Capsules Formed in Emulsion

Based upon the principles presented in the present invention, emulsions offer unique possibilities for transporting hydrophobic materials in an aqueous medium. Thus, the invention provides for the self-assembly of a super-amphiphile layer around an oil droplet in water, with or without cross-linking of the super-amphiphile. Capsules, similar to polymersome vesicles, can be formed in microemulsions, in which oil droplets are dispersed in water and the amphiphile is used to stabilize the oil-water interface. The preferable amount of oil is 1 to 5% (v/v) in aqueous solution. The amphiphile can be dissolved in either the aqueous or oil phase before mixing. The mass of the added amphiphile depends on the desired size of the emulsion as determined from the following equation:

$$\text{Mass}(m) = 3V_T M_n / (r_v N_A A), \tag{6}$$

wherein $V_T$ is the total volume to be encapsulated, $M_n$ is molecular weight of the amphiphile, $r_v$ is the radius of the microemulsion droplets, $N_A$ is the Avogadro number, and A is the molecular area of the amphiphile at the surface. The factor of three comes from simple geometry.

Relatively monodisperse emulsions were prepared by adding oil to the aqueous phase and filtering several times through polycarbonate filters. The pore size of the filter controls the size of the droplets. Therefore, the size of the microemulsion is limited only by the availability of the polycarbonate filters with desirable pore sizes. Currently, pore sizes of commercially available filters range from 0.01 to 20 μm (Osmonics, Livermore, Calif., USA).

Figure 13:
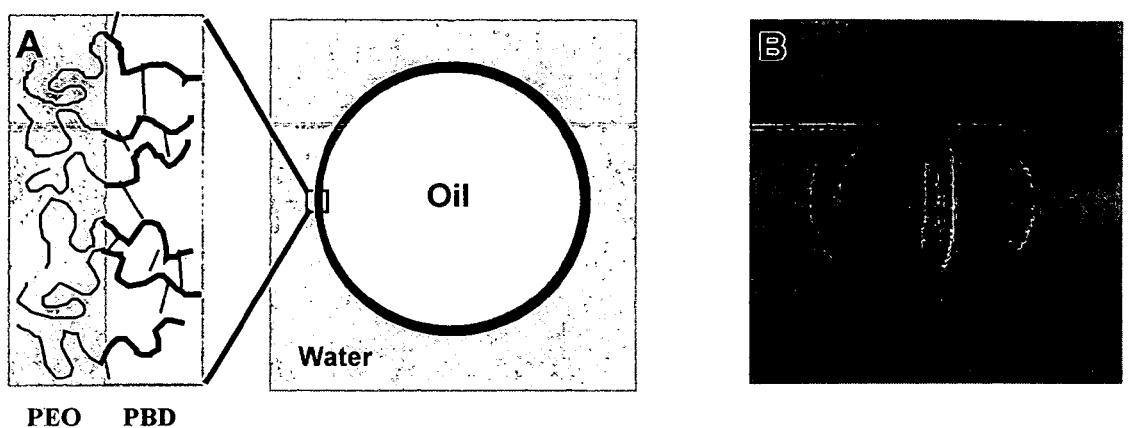
FIG. 13 depicts stabilization of a micro-emulsion by interfacial cross-linking.

The amphiphilic molecules form a stabilizing monolayer at the oil-water interface. When part or all the amphiphile contains a cross-linkable moiety, the surface of the microemulsion was efficiently cross-linked by the generation of free radicals as described above for the cross-linking of vesicles (FIG. 13). This cross-linking further stabilized the droplets against their natural tendency to coalesce with other droplets. For example, the method was successfully used to stabilize 10 μm kerosene droplets in aqueous solution with a PEO—PB of molecular weight $M_n$=8,100 and hydrophilic volume fraction of 62% (see FIG. 13A, wherein PEO is shown facing the water, and PB is shown facing the oil).

After completion of the redox reaction, e.g., ($K_2S_2O_8$/$Na_2S_2O_5$/$FeSO_4$·$7H_2O$ as described above), the 10 μm droplets were of a size that could be aspirated without fragmentation into a micropipette with radius $R_p$=4 μm by negative pressure, $\Delta P$=0.200 atm (FIG. 13B). The resulting droplets of oil are well suited for encapsulation and transport of hydrophobic material, and the amphiphile capsules prepared using the emulsion method offer exciting new opportunities as, e.g., artificial blood cells. For example, perfluorocarbon emulsions have already shown promise as oxygen-carrying blood substitutes.

In sum, polymersomes, enable direct measurements of the material properties of lamellae and permit characterization of membrane assembly. The preparation methods of the present invention provide additional ways to "engineer" bilayer membranes. As compared with lipids, the increased length and conformational freedom of polymer chains of this invention, not only provide a basis for enhanced stability, toughness and reduced permeability of membranes, but also provide a rich diversity of block copolymer chemistries (molecular weights, block fraction, block architecture), thereby furnishing a plethora of novel, artificial membranes and tissues, soft biomaterials and biomimetic structures, controlled-release vehicles and systems for engineering and biomedical applications.

All patents, patent applications and publications referred to in the present specification are also fully incorporated by reference.

While the foregoing specification has been described with regard to certain preferred embodiments, and many details have been set forth for the purpose of illustration, it will be apparent to those skilled in the art that the invention may be subject to various modifications and additional embodiments, and that certain of the details described herein can be varied considerably without departing from the basic principles of the invention. Such modifications and additional embodiments are also intended to fall within the scope of the appended claims.

The invention claimed is:

1. A polymersome vesicle consisting essentially of a semi-permeable, thin-walled encapsulating membrane, having the capacity to encapsulate at least one encapsulating therein, wherein the membrane is formed in an aqueous solution without use of organic solvent, wherein the membrane comprises one or more wholly synthetic, super-amphiphilic molecules that are polymeric, having a number average molecular weight >1400, and wherein at least one super amphiphile molecule is a block copolymer, and wherein the polymeric molecules directly self assemble into vesicles without need for post-assembly polymerization or cross-linking.

2. The polymersome vesicle of claim 1, wherein all of the super-amphiphilic molecules comprising the membrane are block copolymers.

3. The polymersome vesicle of claim 1, wherein the super-amphiphilic molecules of the membrane comprise at least one multi-block copolymer.

4. The polymersome vesicle of claim 1, wherein the super-amphiphilic molecules of the membrane comprise at least one diblock copolymer.

5. The polymersome vesicle of claim 1, wherein the super-amphiphilic molecules of the membrane comprise at least one triblock copolymer.

6. The polymersome vesicle of claim 1, wherein the at least one polymer of the block copolymer is selected from the group of polymers consisting of polyethylene oxide (PEO), poly(ethylethylene) (PEE), poly(butadiene) (PB), poly(styrene) (PS) and poly(isoprene) (PI).

7. The polymersome vesicle of claim 1, wherein the polymersome is biocompatible.

8. A method of encapsulating at least one encapsulatable material in-vitro into the polymersome vesicle of claim 1, comprising exposing the polymersome and at least one material to be encapsulated therein to one or more chemicals or to propagated light, X-ray or UV waves, IR irradiation, sound, ultrasound, heat, or motion to effect encapsulation into the polymersome, thereby moving the at least one material to be encapsulated from an environment immediately surrounding the polymersome into the polymersome.

* * * * *